(12) United States Patent
Spena et al.

(10) Patent No.: US 6,483,012 B1
(45) Date of Patent: Nov. 19, 2002

(54) METHODS FOR PRODUCING PARTHENOCARPIC OR FEMALE STERILE TRANSGENIC PLANTS AND METHODS FOR ENHANCING FRUIT SETTING AND DEVELOPMENT

(75) Inventors: Angelo Spena, Verona (IT); Heinz Saedler, Cologne (DE); Hans Sommer, Pulheim (DE); Guiseppe Leonardo Rotino, Lodi (IT)

(73) Assignee: Max-Planck-Gesellschaft zur Förederung der Wissenschaften e.V., Berlin (DE)

( * ) Notice: Subject to any disclaimer, the term of this patent is extended or adjusted under 35 U.S.C. 154(b) by 0 days.

(21) Appl. No.: 09/331,359

(22) PCT Filed: Dec. 19, 1997

(86) PCT No.: PCT/EP97/07202

§ 371 (c)(1),
(2), (4) Date: Sep. 21, 1999

(87) PCT Pub. No.: WO98/28430

PCT Pub. Date: Jul. 2, 1998

(30) Foreign Application Priority Data

Dec. 20, 1996 (EP) ............................. 96120645
Mar. 12, 1997 (EP) ............................. 97104156
Apr. 9, 1997 (EP) ............................. 97105843

(51) Int. Cl.$^7$ ................. C12N 15/29; C12N 15/31; C12N 15/82; A01H 5/00; A01H 5/10
(52) U.S. Cl. ............. 800/290; 800/278; 800/287; 800/288; 435/69.1; 435/320.1; 435/419; 435/468; 536/23.6; 536/23.7
(58) Field of Search ............... 800/278, 288, 800/287, 290; 435/419, 69.1, 468, 320.1; 536/23.6, 23.7

(56) References Cited

U.S. PATENT DOCUMENTS 4,943,674 A * 7/1990 Houck et al. ............... 800/205

FOREIGN PATENT DOCUMENTS

| EP | 0 412 006 A1 | 2/1991 | ........... C12N/15/82 |
| WO | WO 96/40951 | 12/1996 | ........... C12N/15/82 |
| WO | WO 97/30165 | 8/1997 | ........... C12N/15/82 |
| WO | WO 97/41240 | 11/1997 | ........... C12N/15/82 |

OTHER PUBLICATIONS

Rivka Barg, et al., "Two Approaches to Genetically Engineered Parthenocarpy," *Supplement To Plant Physiology,* 111(2), pp. 161 (1996).

J.J. Estruch, et al., "The Protein Encoded by the rolB Plant Oncogene Hydrolyses Indole Glucosides," *The EMBO Journal,* 10(11), pp. 3125–3128 (1991).

Ove Nilsson, et al., "Indole–3–Acetic Acid Homeostasis In Transgenic Tobacco Plants Expressing the *Agrobacterium rhizogenes* rolB," *The Plant Journal,* 3(5), pp. 681–689 (1993).

Guiseppe Leonardo Rotino, et al., "Genetic Engineering of Parthenocarpic Plants," *Nature Biotechnology,* 15, pp. 1398–1401 (1997).

Zsuzsanna Schwarz–Sommer, et al., "Characterization of the Antirrhinum Floral Homeotic MADS–Box Gene deficiens: Evidence for DNA Binding and Autoregulation of its Persistent Expression Throughout Flower Development," *The EMBO Journal,* 11(1), pp. 251–263 (1992).

Folke Sitbon, et al., "Transgenic Tobacco Plants Coexpressing the *Agrobacterium tumefaciens* iiaaM and iiaaH Genes Display Altered Growth and Indoleacetic Acid Metabolism," *Plant Physiol.,* 99, pp. 1062–1069 (1992).

A. Spena, et al., "Anther–Specific Expression of the rolB Gene of *Agrobacterium rhizogenes* Increases IAA Content in Anthers and Alters Anther Development and Whole Flower Growth," *Theor. Appl. Genet.,* 84, pp. 520–527 (1992).

Jedrzej B. Szerszen, et al., "Iaglu, a Gene From *Zea mays* Involved in Conjugation of Growth Hormone Indole–3–Acetic Acid," *Science,* 265, pp. 1699–1701 (1994).

* cited by examiner

*Primary Examiner*—David T. Fox
(74) *Attorney, Agent, or Firm*—Fish & Neave; James F. Haley, Jr.; Grant Kalinowski

(57) ABSTRACT

Described is the use of the promoter region of the DefH9 gene of *Anthirrhinum majus* or of a promoter of a homologous gene displaying the same expression pattern and characteristics for the establishment of parthenocarpy or female sterility in plants, for increasing gynogenesis or for enhancing fruit setting and development. Also described are recombinant DNA molecules comprising a DefH9 promoter in combination with a DNA sequence which upon expression in plants leads to the above mentioned effects. Furthermore, described are plant cells and plants transformed with such recombinant DNA molecules.

33 Claims, 12 Drawing Sheets

**PROMOTER and CONTROLLING SEQUENCES of the *DefH9* gene from *Antirrhinum majus***

AATTCGGCACGAGGTCCCTTTCTATTTTTGCACAAAGCGTCTTTTACTCGTATCAAGAATTTGATTCTAC
TTTATTACTCAAATTCGTCACTTCTCTTACACACACACACACACACACACACACACACACACATATATA
TATTACACTCCAGCCCTTTGTATCTATCCCATCTTTCTCTTATTAATGAATGAACCAATAAATAGACCTCT
AACAAATACAGTTTGAGCAGGCTGGTTGTTTAATAAAATTAATGCTGGTTGTTAATTTAAACTGACATTGT
TTTTGCTCAGACACGGCAACCTCTATAGTACAGTTTCTTCTTAGTATTGAAAATTTAGTTGTGGATTTTTT
TTTTAAGAAATACAATTTACAGCTATAATGTACAATGCCAAGAACTACAGTTATTTTTTTAATCACTGAAAT
GCTTATATATATTAAAAAGAATCTAAAGAGGGTCAGCGCAATTATTAACTTTTTTCTCCTGAACATTGACC
AAACTTAATATGTGAAAACAACAAAAATTCATAAGGCAGAGGGATCATAGTACAACATTGGATTTGGTGT
GTTACATATAATTAATTAGACCAGGTCCCCTCAGTTACTATTCATGTAAAACTTGTACTTATTGAGCAGAT
ATTTCTAAAGCTATACCCTAACCAATCAAACTGGACTACGTACCCTATCCTTTCAAAGGTTTTTTTTTTTT
TTTTTTTTCCTCCCAATTAAATTCGCGTGCACAAACAAAACTATATTAATCAGGTAAGAAAATTGCGACTC
ATATAGTTTTCCATGTTAAAAAAAGTGAGATATACCAATTAATTTCACTGCATGCAAACAATATGCATGCC
CAAGTAAGTTATGGAAGTTCTTTTTCCTATATATAGAAACCAACTTAGCAATCTCTATTTCATATATATATA
TAAACAGTTAATTTATTAGTCTCTGAAAAAATTTAATGCAAGTCGATCGGTTTACAAAAAGTATATATGGG
CAATTAAATTGGAACAATAAGTGTCACGCTAGTTTTGAATCAGCTCATGATCATGACAGGATACTCCATA
AGTTTTCATTAAATCTTAGCTGATATATCTAGTTAGGAGCCGTAGATATATAAGAAGGTAACGATTAAATT
GAAACGATAAGTTACATATTATAATATGTCATTTGTATGATTACTTGATTAGGGTATTAGATTGTGCAGCC
TAATGTATTGTACATTAATTCCCTCCTTTCTAACACGGTTCAACTCATGTATAAAATTTTAGGGGTATTAC
CGATAATTCACGTAAAATTATAATTATGATTGTATTCCTAATAAAAATAGTCCACTAATGTACGCAATTGC
AATTGACTCATTGAACATATTGAAAAACTCCCGGTTCGGCATGCTGCCTCAAGACACGGTCTCTCTAAC
GAACCGAATACACAAATTTATGTGTGTTTCGTCGCTTTTTGCGTGTACCATATAATCGGATTGCTTCATAA
AGGGAGGTTAAATAAACTCTGCTACAATTCAACCTCAGTAGATTATTTGATGCGCCAAGCAACAACGGTT
ATATTATGCAACGAAGTACGAGCTTATCAAATTACATTGTTTCGGGCTCATATCTCTAATAGTCCTACTAA
ACCCCGTAATATATAGCAAAATAATAGTACACAGATTCAAAAATAAAACCCCTTAATATGAGGCTACTATC
GACTACCAAAGGTAATACACATCATAATCAATGTTCCAAAAACATAATTAAAAACAGTTAATTATATTAAG
TCCATGTAGTTTTTAAAATTAAGAGATATATTCAAGTCTCAACAAACACATGCAAGTTACATATCTAGTGA
CTTCTGCGTGTAATGCACCTAACAACAAACCCTAACCAGCCAAAACTAAAAAATATATATATGTAACACA
GTAACAGAATATATTCACCTCCCAAAATCCCATTATTTATAAGAATTTTTTTAAAGTTCTTGGTAATTAATT
CCCGCATGCAAACTCACCTAATTTTTTTCTATGCTCACCTGGGATTTAATAATTATAAAAAAGACATTAAA
ACATTTTACAAAGTCATGCAACAATCCTTTAAAAAAAAAAAAAAAAAAAAGCTGAAGCAATTACTATATTTG
GTGCGAATTCTCCCTGCAGAGCTGATAATAATCACACCACGCCTGGTACAAAAATGGAAATGGTGTCAT
TTTCTTGGCCAGCTCTTCTATCTCTCCTTCTTTTGCACTACATAAGATAAAGCTAGGTATATACAAAG\* AA
AGAAAATAAGTATATCAAAATAATTAGTGGTGTGATTATTTAATATTTATTTGATCATTCAAGAAACTAAAA
ACTTTGAAGGGATTCTTTGGAACTCGTGTTGAGCTCTCAAAACTCGCCGGAAAATAGAAATATTTTCCGA
ACAAGACAGGTTTGTGAGTCATCATGCAGATCATGAAGATTGTCTAATTATATATTAAAAAAGGAATAAAT
<u>ATTTCTTTAAGTATGGATTGGTTAATTAATTTATTTTTTCCTCTTTATGTTTATGGCACAGTACCAAATGTT</u>
<u>TTCTCTTTGTGCTCAAATTTATGTCAGTTTTTTTTTGTATGTTCTTGTTTAAGCATGGATCTATTGCCATAA</u>
<u>CACATAAAACTTGTTTTTTGGCTTGAAAGATTTAATCTTTCCTCCTATTTTTCATGGGTTTTTTTTTTTTTT</u>
<u>TTTTTTTTATTCATTGACAAGAATGTCAAATCTTAGTATGATTTTTATTTTTATTTGTATGCATGATTTCAA</u>
<u>AAGCTTTTAATTTGCTATCTTCTAGCGCCAAAAACTTGTTTCTACCCTAGGGGACTATGGAACTGAGGGG</u>
<u>AATCTTTGGAAACTTCTGATTTCATTTTGGGCCTTGTTTGTTTTTCTGATTTCTTGTTTTTGGAGGGGACT</u>
<u>TTTATAAAATATGAGCTGTGTAAAGTCGATGAAGGAGGTTTTGACTCTGATCCCTCTTTCAAATTTTGGTT</u>
<u>GAGTTAAGCTTTTGAAGTCATTAAAAAGAGCTATATATATCACTGCCAAGAACTTTGCCAAATAGTTTCAA</u>
<u>GATATAATTTTTTTAGTTCAAAGAACATAGTTTTTTGATCTTGGCTTGTAATGGGGATCCTGCTTTTTTTT</u>
<u>TTTTTTTTTCAGTTCAAATTAATTTCTCATCTTGCTATTCTTGAGGGGCTAATTACAGGATTCTTCAGAAAA</u>
<u>AATCATGTATAAGATTTTCATTATCTTTTTGTACACTATGTATAGATTTTCAGCTGATTGTTTATCAAAGCA</u>
<u>TCCTCTTCAAAAAGTCTTTCTATTTTCAAATTAAAACTATGTCTTCTCTGTGTGTGTTGAATCAAAAGACTT</u>
<u>CCTTTTCTTTTTTTTGCTACAAAGAAAGAAAATCCAGTGTTTGCTTTAGATCTATGATACATTGTTCTCTA</u>
<u>TGATCAAGATTAATAAATCTTATAGTGAGCTTTTTGTTTATTATGATTAGGTTATTTTTCTGAG</u>GTAC

Figure 2

METHODS FOR PRODUCING PARTHENOCARPIC OR FEMALE STERILE TRANSGENIC PLANTS AND METHODS FOR ENHANCING FRUIT SETTING AND DEVELOPMENT

This application is a 371 of PCT/EP97/07202 filed Dec. 19, 1997.

FIELD OF THE INVENTION

The present invention relates to the use of the promoter region of the DefH9 gene of *Antirrhinum majus* and of promoter regions of homologous genes in other species for the highly specific expression of genes in the placenta and/or ovules of plants or tissues derived from placenta or ovules in order to achieve, for example, parthenocarpy, female sterility and for an enhancement in fruit setting and development. The present invention also relates to DNA constructs in which said promoter controls the expression of a DNA sequence which upon expression leads to the above mentioned effects. Furthermore, the present invention relates to transgenic plants genetically modified with such constructs which can develop fruits also in the absence of fertilization (i.e. with parthenocarpic development) or which are female sterile as well as to the fruits of these plants and to the propagation material of these plants.

In the field of crop plants grown for the commercial value of their fruits, there is a great demand for plants able to develop fruits in the absence of fertilization. This is due not only to the absence of seeds (e.g. table grape, melon), but most prominently, to obtain fruits in environmental conditions not favorable for fertilization (e.g. eggplant, tomato; Lipari and Paratore, Acta Hort. 229 (1988), 307–312; Savin, PHM Revue Horticole 374 (1996), 50–52). Methods to achieve parthenocarpic development essentially consist either in using chemically active ingredients, in using mutants conferring parthenocarpic development to the species where they have been selected or by using alterations in chromosome number (i.e. polyploidy). Thus, plants which are suitable for breeding plants with the mentioned desired properties have so far been available only to a limited degree. Indeed, it is common practice for some horticultural plants to treat (i.e. spray) flower buds with synthetic growth factors to cause parthenocarpic development (references above, and: La Torre and Imbroglini, Informatore Agrario 16 (1992), 71–78; Roberts and Hooley, Plant Growth Regulators, Chapman and Hall (New York (1988)). The success of exogenous application of phytohormones relies on their even action on the plant organ, it is labor-intensive and adds extra costs to the production process. Secondly, the chemicals can be transported from the site of application, and so they can affect other parts of the plant or the whole plant.

Plant genetic engineering has recently been applied in order to circumvent the above-mentioned drawbacks connected with the use of mutants or the exogenous application of phytohormones to the plants. For example, Barg, Acts of the III I.S.H.S. Symposium on "In vitro culture and horticultural breeding" Jerusalem, Jun. 16–21 (1996), 13, disclosed the generation of transgenic tomato plants which contain a rolB gene under the control of the TPRP-F1 promoter (from tomato). The use of this promoter leads to the expression of the rolB gene preferentially in the ovary and young fruit. As a result the plants showed parthenocarpic development. However the promoter used displays also a well detectable level of expression in vegetative tissue (i.e. 1.8%, 3.5%, 0.1% in root, stem and leaf, respectively) as compared to expression in the ovary (=100%; Salts et al. (Plant Mol. Biol. 17 (1991), 149–150). Due to this basal level of expression, the plant can also be altered in its physiological processes in vegetative tissues. In a second example, the same TPRP-F1 promoter was used by Szechtman et al., Acts of the III I.S.H.S. Symposium on "In vitro culture and horticultural breeding" Jerusalem, Jun. 16–21 (1996) 32, to drive the expression of the bacterial iaaH gene coding for an indoleacetamide hydrolase able to hydrolyse a number of indoleacetamide analogs, and thus to convert the inactive indoleacetamide (IAM) and naphthalenacetamide (NAM) to the active phytohormones indoleacetic acid (IAA) and napthalene acetic acid (NAA), respectively. The resulting transgenic plants showed parthenocarpic development when sprayed with NAM. This disclosure represents an improvement of the efficiency of parthenocarpic development, but still depends on the exogenous application of chemicals such as NAM. The transgene caused no adverse pleiotropic effects per se, though young plants sprayed with 25 ppm NAM have been reported to exhibit a slight epinastic response (Szechtman et al., loc. cit.). In the same communication Szechtman et al. (1996) proposed that the TPRP-F1-iaaH system will have to be combined with TPRP-F1-iaaM to enable endogenous auxin biosynthesis in the fruit.

However, the TPRP-F1 promoter used in the disclosed chimeric genes, has the drawback that due to its basal level of expression also in vegetative tissue it is also active after transformation and during the regeneration process of transformed cells. Since the expression of the iaaM gene or of genes leading to a higher sensitivity for auxins (like rolB) interferes with the regeneration process, the TPRP-F1 promoter is not suitable to obtain optimal plants transgenic for the iaaM or rolB gene. The reason for this is its constitutive basal level of expression in vegetative tissue. This feature of the promoter hinders the efficient regeneration of plants with an optimum level of expression and unaltered in their vegetative growth. As a consequence either transgenic plants are regenerated which do not express the iaaM gene and/or plants are regenerated with a level of constitutive expression of the iaaM or rolB gene so low to be compatible with regeneration. It is known that the constitutive expression of the iaaM gene has deleterious effects in transgenic plants (Gaudin et al., Plant Physiol. Biochem. 32 (1994), 11–29). Thus, these plants do not represent optimal products since i) they might be altered in their vegetative growth (auxin affects many physiological processes including interactions with environmental and microbial factors) and ii) their level of expression in the ovary might be curtailed and not strong enough to promote parthenocarpic development efficiently. In the case of plants obtained using transformation methods not involving manipulations in tissue culture, the constitutive level of expression in vegetative tissues would furthermore interfere with seed germination and seedling growth. The above described experiments for the generation of transgenic plants are based on the well known fact that developing ovules are a good source of auxins (Archbold and Dennis, J. Amer. Soc. Hort. Sci. 110 (1985), 816–820), and that exogenous auxin can substitute the developing ovules (e.g. the achenes of strawberries) to support growth of the receptacle (Nitsch, Amer. J. Bot. 37 (1950), 211–215; Archbold and Dennis, 1985, loc. cit.) thereby leading to parthenocarpic development. Thus, to mimic the hormonal effects of pollination by plant genetic engineering, the expression of a chimeric gene able to alter auxin content and activity should take place specifically in cells of the female reproductive organs, preferably in the ovules and most preferably also in tissue derived therefrom. This requires a promoter which is highly specific for expression in such cells.

With regard to female sterility there are several reports in the art how to obtain female sterile plants by genetically engineering plants with genetic information which leads to the killing or disabling of cells of the female reproductive organs. These approaches are mainly based on the concept that a highly toxic agent is produced in the cells, such as an RNase, a protease or a bacterial toxin. Alternatively, antisense RNA or a ribozyme against transcripts of essential genes are produced. All these approaches require the highly specific expression of the introduced construct in cells of the female reproductive organ and the absence of expression in other tissues since the expression in other tissues would be deleterious for the development of the plant.

Thus, the technical problem underlying the present invention is the provision of methods and means for the production of transgenic plants which due to the highly specific expression of a transgene in cells of the female reproductive organ, in particular in the placenta and/or the ovule, are female sterile or show a parthenocarpic development or an enhanced parthenocarpic development.

This technical problem is solved by the provision of the embodiments characterized in the claims.

SUMMARY OF THE INVENTION

Thus, the present invention relates to the use of a DefH9 promoter for the expression of a DNA sequence in plant cells for a purpose which requires highly specific expression in the placenta and/or ovule of a transgenic plant and an extremely low level of expression in cells of vegetative tissue. Examples for such purposes are the establishment of parthenocarpy or female sterility by expressing specific DNA sequences in cells of the female reproductive organ of transgenic plants. Further purposes are the increase in the rate of gynogenesis and the production of haploid-double haploid lines or hybridization between distant plant species.

Accordingly, in a first aspect the present invention relates to the use of the promoter region of the DefH9 gene of *Antirrhinum majus* or of a promoter region of a gene homologous to the DefH9 gene of *Antirrhinum majus* and capable of directing placenta and/or ovule specific expression of a DNA sequence linked to it in plants for the establishment of parthenocarpy.

The invention is based on the finding that the promoter region driving expression of the DefH9 gene of *Antirrhinum majus* has an extremely low level of basal activity in tissues other than the placenta and/or the ovule. Thus, this promoter is on the one hand suitable to obtain highly specific expression of a DNA sequence in the above-mentioned tissues of female reproductive organs of plants. This helps to avoid unwanted modifications of other physiological and developmental processes which constitute the drawbacks of the methods known in the art. In order to achieve parthenocarpic development, the basal level of constitutive expression of the introduced chimeric gene which affects, for example, the auxin metabolism has to be as low as possible (i.e. preferentially below detection limit). This aspect is particularly relevant when the genetic information introduced into the plant cells controls the level and activity of growth factors, such as the phytohormones belonging to the auxin type as is the case when trying to establish parthenocarpy by increasing the auxin content or activity.

On the other hand this promoter, due to its extremely low level of basal activity in vegetative tissue helps to circumvent the problems described above which arise when using, for example, the TPRP-F1 promoter. In particular, since the DefH9 promoter is not active during the regeneration of transformed plant cells to transgenic plants, there is no selection for cells which have only a very low level of promoter activity. Thus, this promoter is particularly suited and useful for the use in the generation of transgenic plants which show a parthenocarpic development due to the expression of a foreign DNA sequence specifically in cells of the female reproductive organ, namely in the placenta and/or ovule and most preferably in tissue derived from placenta or ovule, such as the integument of seeds.

In the present invention the term "DefH9 promoter" means the promoter region of the DefH9 gene of *Antirrhinum majus* including regulatory sequences which is capable to specifically direct expression in the placenta and/or the ovules of transgenic plants or in tissue derived therefrom and which does not show a detectable level of basal expression in vegetative tissues. Preferably, the promoter starts to direct expression in these tissues before the onset of anthesis. "Not showing a detectable level of expression" in this context means that expression of a gene linked to a DefH9 promoter cannot be detected in a Northern blot analysis in probes of vegetative tissue. Such a Northern blot analysis can be carried out according to methods known in the art and is preferably carried out as described in the Examples (see below).

The expression of the DefH9 gene occurs very specifically in the placenta and in the ovules during early phases of flower development as shown by in situ hybridization. It is shown in the present invention that the level of expression of the DefH9 promoter in vegetative tissue is below the detection limit of Northern blot analysis (see FIG. 3). The DefH9 (Deficiens homologue 9) gene of *Antirrhinum majus* is described in the Ph. D. thesis of Rolf Hansen (1993, University of Cologne, Faculty of Mathematics and Sciences). This thesis discloses the cDNA sequence as well as the genomic sequence of the DefH9 gene including its promoter region and its regulatory sequences. The DefH9 gene is a MADS box gene, expression of which occurs in early stages specifically in the developing placenta and ovules of the female reproductive organ, and becomes restricted at later stages to the ovules and the vascular bundles of the placenta. The nucleotide sequence of the DefH9 promoter and regulatory regions is depicted in FIG. 2 and also in SEQ ID No. 1. In the sequence the transcription initiation site is located at position 2265. The first intron is located in the transcribed but untranslated leader and corresponds to nucleotides 2418 to 3462 of the sequence given in SEQ ID No. 1.

The term "promoter" refers to the nucleotide sequences necessary for transcription initiation, i.e. RNA polymerase binding, and also includes, for example the TATA box.

The term "regulatory regions" refers to sequences which further influence the level of expression, for example, in the sense that they confer tissue specificity. Such regions can be located upstream of the transcription initiation site, but can also be located downstream of it, e.g. in transcribed but nontranslated leader sequences, especially in introns.

In the present invention the term "DefH9 promoter" is used as comprising a promoter and the regulatory regions necessary to obtain the above described specificity, namely specific expression in the placenta and/or ovule of plants and no detectable expression in the cells of vegetative tissue.

In a preferred embodiment of the present invention the promoter comprises the nucleotides 1 to 2264 of the nucleotide sequence as set forth in SEQ ID No. 1 or a fragment thereof which still confers specific expression in the placenta and/or ovules of transgenic plants. Most preferably, such a fragment comprises besides a promoter furthermore nucleotides 2265 to 3480, which corresponds to the transcribed but untranslated leader sequence of the DefH9 gene of *A. majus* and most preferably comprises the first intron (nucleotides 2418 to 3462). The term "DefH9 promoter" also includes promoter regions and regulatory regions of a gene from the same or another plant species which is homologous to the DefH9 gene of *A. majus* and the promoter region of which has the same tissue specificity as the DefH9 promoter. Such promoters are characterized by an extremely low level of activity in organs and tissues other than cells of the female reproductive organs, namely of cells of the placenta and/or the ovule or of tissue derived from placenta or ovule. Genes homologous to the DefH9 gene of *A. majus* are genes which encode a protein which is structurally or functionally homologous to the DefH9 gene product of *A. majus*. Structural homology preferably means that the coding region of the gene shows a sequence identity to the coding region of the DefH9 gene of *A. majus* of at least 40%, preferably of at least 60% and more preferably of at least 80%. More preferably, the gene homologous to the DefH9 gene of *A. majus* encodes a protein belonging to the family of the MADS box proteins and even more preferred a protein belonging to the AGAMOUS subfamily of the MADS box proteins. Thus, according to the invention promoters from other species can be used that are structurally or functionally homologous to the DefH9 promoter from *Antirrhinum majus*, or promoters that display an identical pattern of expression, in the sense of being not only expressed in the ovules and/or placenta but, and most important, not showing a detectable level of expression in vegetative tissue. It is possible for the person skilled in the art to isolate with the help of the known DefH9 gene from *A. majus* corresponding genes from other plant varieties or plant species. This can be done by conventional techniques known in the art, for example, by using the DefH9 gene as a hybridization probe or by designing appropriate PCR primers. It is then possible to isolate the corresponding promoter region by conventional techniques and test it for its expression pattern. For this purpose it is, for instance, possible to fuse the promoter to a reporter gene, such as luciferase, and assess the expression of the reporter gene in transgenic plants. The present invention also relates to the use of promoter regions which are substantially identical to the DefH9 promoter of *Antirrhinum majus* or to a promoter of a homologous gene or to parts thereof and which are able to confer specific expression in the placenta and/or ovules in plants without detectable expression in cells of vegetative tissue.

Such promoters differ at one or more positions from the above-mentioned promoters but still have the same specificity, namely they comprise the same or similar sequence motifs responsible for the above-described tissue specificity. Preferably such promoters hybridize to one of the above-mentioned promoters, most preferably under stringent conditions. Particularly preferred are promoters which share at least 85%, more preferably 90% and most preferably 95% sequence identity with one of the above-mentioned promoters and has the same specificity.

As described above, the DefH9 promoter or a promoter of a homologous gene which displays the same or a similar expression pattern with a very low basal level of expression in vegetative tissue are particularly useful for the generation of plants showing a parthenocarpic development by genetic engineering. One approach to achieve parthenocarpic development in plants is the increase in auxin content and/or activity in cells of the female reproductive organ of a plant, preferably in the placenta and/or ovule. In general, this can be achieved in different ways. In one embodiment of the present invention an increase in the content and/or activity of at least one auxin in the cells of the female reproductive organ is achieved by expressing in the plants a DNA sequence under the control of the DefH9 promoter, wherein said DNA sequence upon expression leads to an increase in the intracellular content or activity of at least one auxin. One meaning of the term "increase in the auxin content and/or activity" is that the synthesis rate of an auxin is increased. This might be achieved, for example, by increasing the conversion of a metabolite directly into an auxin or alternatively by increasing the synthesis and consequently the concentration of a precursor of an auxin which is then converted into the respective auxin. Another meaning of this term is that the release of conjugated auxins is enhanced or the conjugation of auxins is prevented or reduced.

The term "auxin" comprises in this context naturally occurring and synthetic organic substances acting as a phytohormone in the sense that they promote elongation of shoots and inhibit elongation of roots, preferably in very low concentrations, most preferably already in concentrations lower than $10^{-6}$ M. Preferably, an auxin shows at least one of the following effects on plant development: stimulation of cell division, of cell elongation, and/or of cell expansion, of apical dominance, stimulation of xylem differentiation, stimulation of the cell elongation and cell division activity of the cells of the cambium, stimulation of lateral and adventitious root formation, stimulation of nodulation, of germination, of leaf epinasty, of ovary cell growth, of parthenocarpy, of the formation of female flowers and of leaf expansion. More particularly, the term "auxin" refers to indole acetic acid (IAA) which is most likely synthesized in plant cells from tryptophane via indole-3-pyruvate and indole-3-acetaldehyde, and which is degraded via enzymatically catalyzed oxidation.

However, the term also comprises other naturally occurring compounds which act as an auxin and which are derived from indole or from another compound, for example, the naturally occurring phenyl acetic acid which is a non-indolic auxin or 4-(indole-3-yl) butyric acid. Furthermore, this term comprises compounds from organisms other than plants or chemically synthesized compounds which have at least one of the effects on plant development as listed above. An example for such a compound is (2,4-dichlorophenoxy)-acetic acid (2,4-D).

In a preferred embodiment the DNA sequence linked to a DefH9 promoter codes for a polypeptide which is naturally involved in the biosynthesis of at least one auxin in plant cells. The expression of the DNA sequence in plant cells then leads to an increase in the biological (for example, enzymatic) activity of this polypeptide and consequently to the increase of the content and/or activity of at least one auxin in the cells. Thus, in principle, by this embodiment it is contemplated that the auxin content and/or activity can be increased in plant cells by increasing the biosynthesis of at least one auxin due to a stimulation/acceleration of a biosynthetic pathway which naturally occurs in plant cells.

In another preferred embodiment the DNA sequence linked to a DefH9 promoter codes for a protein which is naturally not expressed in plant cells and which upon expression in plant cells leads to the synthesis of at least one auxin or a precursor of an auxin from a metabolite present in plant cells. Genetic information which may be used in this regard is, for example, present in the genomes of several bacteria. For instance, in many cases of bacteria-induced phytopathogenesis, alterations of hormone biosynthesis, content and activity play an important role in the interaction between plants and bacteria. Thus, in a more preferred embodiment of the present invention the DNA sequence linked to the DefH9 promoter codes for a bacterial protein, namely a protein which leads in plant cells to the increase of the content or activity of at least one auxin. Preferably said DNA sequence codes for a protein of a bacterium from the genus Pseudomonas or Agrobacterium. More preferably, said DNA sequence codes for a protein of *Pseudomonas syringae* or of *Agrobacterium rhizogenes* or tumefaciens. One example of a gene which is preferably used for the purpose of the present invention is the iaaM gene of *Pseudomonas syringae* pv. savastanoi, the etiological agent of plant tumors in olive or oleander trees (Spena et al., Curr. Opinion in Biotechnology 3 (1992), 159–163; Gaudin et al., 1994; loc. cit.). The neoplastic development is caused by phytohormones synthesized by the bacteria, which are then secreted into the surrounding tissues and cause uncontrolled growth of plant cells. Among the genes involved in the pathogenesis of this type of tumour, the iaaM gene codes for the indoleacetamide monooxygenase, and it is responsible for converting by oxidation the amino acid tryptophan to indoleacetamide. Indoleacetamide has no particular auxin activity, but it is slowly converted, either chemically or enzymatically, by plant hydrolases to IAA, the major form of auxin in plants. Expression of the iaaM gene in transgenic plants is able by itself to cause modification of hormone metabolism and activity, and consequently to modify plant biochemical and developmental processes (Sitbon et al., Plant Physiol. 95 (1991), 480–485). Thus, in order to avoid constitutive expression which might interfere with the regeneration of transgenic plants from tissue culture and to avoid the possibility that transgenic plants are either altered in their vegetative growth and/or express only a low level of expression compatible with the regeneration process, the iaaM coding sequence is, according to the present invention, placed under the control of a DefH9 promoter.

The present invention demonstrates that the iaaM gene of *Pseudomonas syringae* is able to cause parthenocarpic development in plants when driven by the DefH9 promoter. It is furthermore shown that the temporally and spatially precise and specific control of expression of the iaaM gene plays a crucial role in the genesis of parthenocarpic development. Expression under the highly specific and tightly regulated DefH9 promoter and controlling sequences allows the regeneration of transgenic plants unmodified in their vegetative growth, but modified in fruit setting and development. On the contrary, a basal level of expression of the iaaM in vegetative tissues is not compatible with regeneration of transgenic plants unmodified in their vegetative growth and still expressing the iaaM gene with optimum strength in the desired tissue or organ. The iaaM gene from *Pseudomonas syringae* subsp. savastanoi is known and its sequence has been published (Yamada et al., Proc. Natl. Acad. Sci. USA 82 (1985), 6522–6526). According to the invention genes homologous in function to the iaaM gene of *P. syringae* might be used for the purpose of this invention. Such genes which are preferably also homologous with respect to the nucleotide sequence can be isolated by the person skilled in the art using known methods, e.g., the screening of cDNA or genomic libraries with probes designed on the basis of the iaaM gene of *P. syringae* and subsequently testing the gene product for its biological activity. Such genes with an activity similar to that of the iaaM gene product of *P. syringae* have been cloned, for instance, from some strains of Agrobacteria (i.e. *A. tumefaciens* and rhizogenes; see, for instance, Klee et al., Gene Dev. 1 (1987), 86–96; White et al., J. Bacteriol. 164 (1985), 33–44; Cardarelli et al., Mol. Gen. Genet. 208 (1987), 457–463).

The experimental data provided by the present application furthermore show that the expression of the iaaM gene under the control of a DefH9 promoter has the unexpected effect that these plants show fruit setting and fruit development even under conditions which represent very adverse climatic conditions for eggplant fertilization and fruit development. Thus, the present invention provides evidence that the expression of DNA sequence leading to an increase in auxin concentration and/or activity specifically in cells of the female reproductive organs of plants can lead to fruit setting even under adverse climate conditions. This means that in this way an enhancement of fruit setting and fruit development is achieved. By this it is meant that in comparison to non-transformed plants the transgenic plants of the present invention are able to set fruit (with or without pollination) and to develop them under climatic conditions which in non-transgenic plants would not allow fertilization and/or fruit development.

In another preferred embodiment of the present invention the DNA sequence the expression of which is driven by the DefH9 promoter is the rolB gene from the A4 Ri plasmid of *Agrobacterium rhizogenes*, the etiological agent of the hairy-root disease (Spena et al., 1992; loc. cit.; Gaudin et al., 1994; loc. cit.) or a gene from another source which is functionally equivalent to the rolB gene. The rolB gene is able by itself to alter plant growth. It codes for a protein possessing β-glucosidase activity which might hydrolyse the inactive indolethanol-β-glucoside (IEG) releasing the active auxin indolethanol from the inactive glucoside. This undisclosed hypothesis predicts that this gene does not directly participate in the synthesis of transportable growth factors, but that it releases indolethanol from the inactive glucoside. Indolethanol might act by itself or it might be converted to IAA, the major form of auxin in plants. The sequence of the rolB gene from Ri plasmid A4 of *A. rhizogenes* has been published by Slightom et al. (J. Biol. Chem. 261 (1986), 108–121) and a detailed description has been given by Spena et al. (EMBO J. 6 (1987), 3891–3899). Genes with similar activity have been cloned from some other strains of *Agrobacterium rhizogenes*, and related sequences could be cloned from the genomes of some plant species (e.g. *Nicotiana glauca*). The present invention provides evidence that the rolB gene is not able, in all cases, to trigger parthenocarpic development by itself, at least not in tobacco. Thus, the rolB gene under the control of a DefH9 promoter is preferably used in plants which show on their own a parthenocarpic development under specific circumstances, for example, under specific environmental conditions. In these cases the occurrence of parthenocarpic development can be increased by expressing the rolB gene under the control of a DefH9 promoter.

In a preferred embodiment of the present invention, the rolB gene and the iaaM gene are used in combination to achieve parthenocarpic development. This might, for example, either be done by introducing the two genes simultaneously or by subsequently transforming plants with these genes. Alternatively, two plants, one of which comprises the iaaM gene under the control of a DefH9 promoter and the other which comprises the rolB gene under the control of a DefH9 promoter may be crossed. In these cases it is possible that, even if expression of the DefH9-rolB gene itself is not able to cause parthenocarpic development in all plants of interest, it can increase parthenocarpic development, preferably in conjunction with the DefH9-iaaM chimeric gene. This embodiment is preferred, inter alia, for the following reason. Experimental results indicated that the rolB gene product is a β-glucosidase which might hydrolyze the inactive indolethanol-β-glucoside and therefore releasing indolethanol, a natural auxin. An increase of IAA is followed by an increased conversion of IAA to indolethanol, which is in turn converted to indolethanol-β-glucoside. Thus, plants transgenic, for instance, for the DefH9-iaaM gene would have an increase not only in IAA but also in the content of the inactive indolethanol-β-glucoside providing the substrate for the rolB gene product within the ovary. Thus, the expression of the rolB gene in the same tissues will hydrolyse indolethanol-β-glucoside to the active auxin indolethanol (which in turn can be converted back to IAA; Cohen and Bialek, in "The Biosynthesis and Metabolism in Higher Plants, Eds. Crozier and Hillmann, Society for Experimental Biology Seminar 23 (1984), 165–181). Thus, the use of the DefH9-rolB construct will reinforce the auxin effect of the DefH9-iaaM gene by increasing primarily the indolethanol content. A practical consequence of this is the possibility to screen DefH9-rolB transgenic plants to be used in crosses for their capacity to develop parthenocarpic fruits by chemical treatment of the flower buds with indolethanol. The exogenously supplied indolethanol will have a transient action due to its conversion to the inactive indolethanol-β-glucoside in normal and not expressing transgenic plants, however the expression of a sufficiently high level of the rolB protein will hydrolyse the inactive glucoside to the active aglycone. Consequently the two genes would act in two different ways to increase auxin content and activity: (1) the DefH9-iaaM chimeric gene will increase the content primarily of IAA via indoleacetamide, (2) the DefH9-rolB will have an auxin effect by releasing primarily indolethanol from its glucosides. Thus, its effect will be limited only to plants having a high content of indolethanol-β-glucoside. A higher content in indolethanol-β-glucoside can be achieved either by chemically adding IAA or indolethanol, or in transgenic plants by expressing the iaaM gene.

In a further preferred embodiment of the present invention the DNA sequence expression of which is driven by a DefH9 promoter is one coding for indolepyruvate decarboxylase. Indolepyruvate decarboxylase is the key enzyme in the indole pyruvic pathway of IAA synthesis in which IAA is synthesized from tryptophane. The conversion of indolepyruvic acid is in this pathway the rate limiting step. A DNA sequence encoding a suitable indolepyruvate decarboxylase has been cloned, for example, from Enterobacter cloacae (see, e.g., Koga et al., Mol. Gen. Genet. 226 (1991), 10–16).

The most widespread auxin present in plants, IAA, is mainly conjugated through its carboxyl group to a variety of amino acids, peptides and carbohydrates. The conjugates represent approximately 95% of the IAA present in the cells. It is assumed that these conjugates allow rapid alteration of free IAA concentration. Thus, another approach to increase the auxin content and/or activity in cells of the female reproductive organs of plants would be to express under the control of a DefH9 promoter a DNA sequence which upon expression leads to an increased release of an auxin, for example, of IAA, from its conjugated form(s) or to a decrease of the conversion of free auxin into a conjugated form. An example for such a DNA sequence is a DNA sequence which hydrolyses the conjugates between IAA and an amino acid, a peptide or a carbohydrate.

In a preferred embodiment the DNA sequence, the expression of which is driven by a DefH9 promoter, is the ILR1 gene of plants. The protein encoded by an ILR1 gene has aminohydrolase activity and releases IAA from conjugates with amino acids. ILR1 genes are known from different plants, for example, from *Arabidopsis thaliana* (Bartel and Fink, Science 263 (1995), 1745–1748; GenBank accession no. U23794). DNA sequences encoding proteins with a similar enzymatic activity may be also obtained from bacteria. Further examples are ILL1 and ILL2 genes coding for ILL1 and ILL2 proteins, respectively. Such DNA sequences have been isolated, for example, from *Arabidopsis thaliana* and are available under GenBank accession numbers U23795 and U23796, respectively.

As mentioned above, another possibility to increase auxin content and/or activity in plant cells is to reduce the rate of conversion of free IAA into its conjugates. This may be achieved by inhibiting expression of genes coding for proteins catalyzing this conversion. Possible approaches are, for example, the expression of an antisense RNA, a ribozyme or of a specific inhibitor. A protein catalyzing such a reaction is, for example, the protein encoded by the iaglu gene of maize. The corresponding DNA sequence has been cloned (see, for instance, Szersen et al., Science 265 (1994), 1699). Also possible is the reduction of the degradation rate of an auxin by inhibiting the expression of the enzymes which are involved in the degradation of this auxin, for example, of IAA. A further possibility to increase auxin content and/or activity is the inhibition of its transport.

Another meaning of the term "increase in the auxin content and/or activity" is that the activity or sensitivity of an auxin receptor is increased. Thus, it is, for example, possible to express in plant cells under the control of the above-described promoters a protein which is a receptor of auxin and thereby increase the biological activity of auxin. It is also possible to express auxin receptors with a higher sensitivity for auxin. This would also lead to an increase in the biological activity of auxin.

Another approach to establish parthenocarpy in plants is the increase of the content and/or activity of at least one gibberellin in the cells of the female reproductive organ. This might be achieved, for example, by overexpression of genes coding for proteins involved in the biosynthesis of gibberellins in plants. Such genes are described, for example, in Sun et al. (Plant Cell 4 (1992), 119–128) and Bensen et al. (Plant Cell 7 (1995), 75–84).

The above described high specificity of activity of the DefH9 promoter in the placenta and/or ovules of plants makes it also a useful tool for the generation of female sterile plants which are of relevance, for example, in the generation of hybrid seeds. Thus, in another aspect the present invention relates to the use of the promoter region of the DefH9 gene of *Antirrhinum majus* or of a promoter region of a gene homologous to the DefH9 gene of *Antirrhinum majus* and capable of directing placenta and/or ovule specific expression of a DNA sequence linked to it in plants for the establishment of female sterility. As described in EP-A1 0 412 006, female sterility can be achieved by expressing specifically in cells of the female reproductive organs of a plant a so-called "female-sterility DNA", i.e. a DNA which upon expression significantly disturbs adversely the proper metabolism, functioning and/or development of a cell of a female reproductive organ. Preferably said DNA leads upon expression in a cell to cell death. Examples for such DNA sequences, which in combination with the DefH9 promoter region might be used to establish female sterility in plants are: DNases (e.g. endonucleases such as restriction endonucleases), RNases (e.g. Barnase or RNase T1), proteases (e.g. trypsin or papain), glucanases, lipases, lipid peroxidases, plant cell wall synthesis inhibitors or bacterial toxins which are toxic to plant cells (e.g. botulin, diphteria toxin etc.). Other examples are DNA sequences which encode an antisense RNA molecule of a transcript of a gene normally expressed in the plant cells. This approach is described, for example, in EP-A 0 223 399. The transcribed antisense RNA inhibits the translation of a corresponding transcript naturally occurring in plant cells. DNA sequences which might be used in this regard comprise preferably those which encode for RNA or proteins which are essential for plant cell functioning, e.g. rRNA genes. Another example for a DNA sequence which might be used as a "female-sterility-DNA" is a DNA sequence which encodes a ribozyme capable of highly specifically cleaving a given target sequence. Such a target sequence is again preferably a transcript of a gene the product of which is essential for plant cell functioning.

As is evident from the above, the specificity of expression and the undetectable constitutive level of expression in vegetative tissue play a crucial role in the generation of transgenic plants unaltered in their vegetative growth and yet displaying parthenocarpic development or female sterility. The DefH9 gene is among the flower-specific genes tested so far, the only one displaying an undetectable level of expression in vegetative tissues. This requirement is essential when using a gene the expression of which influences the auxin content and/or activity in plants or leads to the killing or disabling of cells. For example, an increase of auxin content and activity within the ovary achieved by ovule-specific expression is bound to mimic the exogenous subministration of auxin used in horticultural practice. However, even a very low basal expression within vegetative tissue is bound to interfere with plant regeneration and/or plant growth. A modification of vegetative growth, however, is an undesired trait in horticultural and fruit crops.

In yet a further aspect, the present invention also relates to recombinant DNA molecules comprising a DefH9 promoter and linked thereto at least one DNA sequence which leads when expressed in plants to the increase of the content and/or activity of at least one auxin in the cells. Such a recombinant DNA molecule comprises in general furthermore a transcriptional termination region at the 3' end of said DNA sequence.

In a preferred embodiment the promoter used in such a recombinant molecule comprises the nucleotide sequence as set forth in SEQ. ID No. 1 or a fragment thereof which still confers specific expression in the placenta and ovules of transgenic plants.

The DNA sequence linked to said promoter in such a construct is preferably one of the DNA sequences mentioned above in connection with the use of a DefH9 promoter for the generation of plants showing parthenocarpic development.

In a further aspect, the present invention also relates to recombinant DNA molecules comprising a DefH9 promoter and linked thereto at least one DNA sequence which leads when expressed in plants to the killing and/or disabling of cells of the female reproductive organ of the plants thereby resulting in female sterility. Such a recombinant DNA molecule comprises in general furthermore a transcriptional termination region at the 3' end of said DNA sequence.

In a preferred embodiment the promoter used in such a recombinant molecule comprises the nucleotide sequence as set forth in SEQ. ID No. 1 or a fragment thereof which still confers specific expression in the placenta and ovules of transgenic plants. The DNA sequence linked to said promoter in such a construct is preferably one of the DNA sequences mentioned above in connection with the use of a DefH9 promoter for the generation of plants showing female sterility.

Furthermore, the present invention also relates to host cells transformed with a recombinant DNA molecule as described above comprising a DefH9 promoter and linked thereto a DNA sequence which leads when expressed in plants to the increase of the content and/or activity of at least one auxin in the cells. The host cells can be prokaryotic, for example, bacterial, or eukaryotic, for example fungal or animal cells. In a preferred embodiment, the host cells are plant cells. Thus, the present invention also relates to transgenic plant cells transformed with and genetically engineered with a recombinant DNA molecule comprising a DefH9 promoter and linked thereto a DNA sequence which leads when expressed in plants to the increase of the content and/or activity of at least one auxin in the cells. Such cells are characterized by the feature that they contain stably integrated into their genome a recombinant DNA molecule as described above.

In a preferred embodiment of the present invention the plant cells are transformed with an iaaM gene as well as with a rolB gene, both under the control of a DefH9 promoter.

The present invention also relates to transgenic plants comprising plant cells according to the invention. Such plants can show parthenocarpic development due to the increase in auxin content and/or activity without alterations of their vegetative growth. This last feature is particularly relevant and it is due to the absence of detectable expression in vegetative tissue of the DNA sequence linked to the DefH9 promoter. Preferably the plants according to the invention show at least one of the following features:

a) parthenocarpic development (i.e. fruit development in the absence of fertilization);
b) seedless parthenocarpic fruits;
c) fruits with seeds when pollinated;
d) high specific expression, within the ovary, in the placenta, and in the ovules, and preferably also in tissue derived from the ovules or the placenta;
e) no expression in other tissues as deduced from the detection limit of Northern blot analysis with probes labeled at a specific activity of approximately $2 \times 10^9$ cpm/microgram of DNA;
f) an enhancement of fruit setting and/or development in comparison to corresponding non-transformed plants.

The present invention also relates to parts of the plants according to the invention which parts comprise the above-described cells. In particular, the present invention relates to the fruits of these plants as well as to any kind of propagation material, for example, seeds, seedlings or cuttings.

Furthermore, the present invention also relates to host cells transformed with a recombinant DNA molecule comprising a DefH9 promoter and linked thereto a DNA sequence which leads when expressed in plants comprising such cells to the killing or disabling of cells of the female reproductive organs of plants so as to render the plant female sterile. The host cells can be prokaryotic, for example, bacterial cells, or eukaryotic, such as fungal or animal cells. In a preferred embodiment, the host cells are plant cells. Thus, the present invention also relates to transgenic plant cells transformed with and genetically engineered with a recombinant DNA molecule comprising a DefH9 promoter and linked thereto a DNA sequence which leads when expressed in plants comprising such cells to the killing or disabling of cells of the female reproductive organs of plants so as to render the plant female sterile. Such cells are characterized by the feature that they contain stably integrated into their genome a recombinant DNA molecule as described above.

The present invention also relates to transgenic plants comprising plant cells as described above. Such plants show female sterility due to the expression of the DNA sequence linked to the DefH9 promoter in cells of the female reproductive organs.

Furthermore, the present invention relates to parts of the above-described plants which comprise plant cells according to the invention and, in particular, to propagation material, for example, pollen, cuttings etc.

Plants according to the invention can belong to any desired plant species, preferably used are plants of a family selected from the group consisting of Solanaceae, Cactaceae, Papilionaceae, Actinidiaceae, Cucurbitaceae, Rubiaceae, Moraceae, Rutaceae, Vitaceae, Ebenacaeae, Crassularaceae, Rosaceae, Drupaceae, Passifloraceae, Caricaceae, Ericaceae, Gramineae, Cruciferae, Cariofillaceae, Amaryllidiaceae, Iridaceae, Leguminosae, Liliaceae, Paeoniaceae, Papaveraceae, Primulaceae, Scrophulariaceae, Violaceae, Malvaceae and Graminaceae or from the species Actinidia sinensis. Plants derived from eggplant, tomato, melon or watermelon, cucumber, citrus species, pepper, strawberries, grapes, apple, pear, cherry or olive are especially preferred. In principle both dicotyledons and monocotyledons are suitable starting materials for the preparation of the plants of the invention.

The above described transgenic plants of the invention can be used as a source of explants (i.e. ovary and/or ovules) for the production of haploid or double-haploid gynogenetic plants. Auxins are growth factors included in the media employed to obtain in vitro gynogenetic callus or embryos and, then, plants. The specific expression of appropriate chimeric genes in the ovules and placenta of the transgenic plants, for example, the DefH9-iaaM chimeric gene by itself, the DefH9-rolB chimeric gene by itself or a combination of the iaaM and rolB coding regions under the control of DefH9 sequences, ensures an increase of auxins which allows either to improve the frequency of gynogenetic plants produced in the plant species where this technique is currently used or to widen the number of species where gynogenesis might be used. An increase of auxin content and activity within the ovary achieved by ovule-specific expression improves also the recovery of gynogenetic plants following pollination with incompetent pollen by reinforcing the stimulation of the haploid cells division in the embryo sac otherwise caused only by pollen tube growth and fertilization (for a review see: Keller and Korzum, in: Jain, Sopory and Veilleux (Eds); In vitro haploid production of higher plants, Vol. 1 (1996), 217–235; Kluwer Academic Publishers; The Netherlands). The above mentioned mechanism of ovule-specific gene expression of iaaM and/or rolB coding regions will exert a general positive effect on the frequency of viable embryos formed following sexual hybridization through in vitro stigmatic/placentar/ovular/pollination or gametic fusion/fertilization aimed at hybridization between distant plant species. As reported by Bhojwani and Raste, in; Jain, Sopory and Veilleux (Eds); In vitro haploid production of higher plants, Vol. 1 (1996), 237–262; Kluwer Academic Publishers; The Netherlands). most of the culture media employed contain auxins as growth factor to stimulate zygote division. The transgenic plants of the invention can further be used for breeding plants with parthenocarpic development, or to increase by breeding the expressivity of the parthenocarpic trait in varieties showing partial parthenocarpic development. The transgenic plants can be also used as a source of material for gynogenesis and/or in vitro fertilization.

The transgenic plant cells and plants can be prepared according to conventional methods known in the art. In particular, the plants can be produced by any of the following processes:

1. Transformation of plant protoplasts or plant explants with *Agrobacterium tumefaciens* bacteria or *Agrobacterium rhizogenes* bacteria which contain a plasmid carrying a recombinant DNA molecule according to the invention or combinations of at least two recombinant DNA molecules of the invention.
2. In planta transformation by using Agrobacterium strains harbouring the aforementioned constructs to infect plants.
3. Electroporation of plant protoplasts, tissues or organs.
4. Bombardment of plant tissues or organs by using particles coated with the aforementioned recombinant constructs.
5. Plant protoplast uptake of the aforementioned recombinant constructs by using chemical methods (e.g. PEG).
6. Microinjection of the aforementioned recombinant plasmids into plant protoplasts, meristem, microspore, pollen, ovule, tissue or organ.
7. Fertilization of plants with a mixture of pollen and plasmids carrying any of the aforementioned.
8. Exposure of whole plantlets or seeds to Agrobacteria harbouring any of the aforementioned constructs.
9. Introgression of whole or parts of chromosomes containing the aforementioned recombinant constructs.
10. Fiber carbide plant transformation by using the aforementioned constructs.
11. Fertilization of plants with pollen transformed with any of the aforementioned constructs by means of direct or mediated transformation.

In case that it is intended to introduce combinations of the aforementioned constructs of the invention into the plant cells or plants, the combination can be achieved: (i) by co-transformation of independent constructs; (ii) by harbouring on the same construct both chimeric genes (i.e. DefH9-iaaM and DefH9-rolB genes); (iii) by building a bicistronic mRNA containing an internal entry site for ribosomes between the two open reading frames in order to ensure that both are expressed under the control of the DefH9 promoter and controlling sequences; or (iv) by sexual and asexual hybridization of two independent transgenic plants containing either, for example, the DefH9-iaaM or DefH9-rolB genes.

BRIEF DESCRIPTION OF THE FIGURES

FIG. 2: DNA sequence of the promoter and regulatory sequences of the DefH9 gene of *Antirrhinum majus* used for the construction of the plasmids as described in the examples

FIG. 10 shows transgenic eggplants transformed with the DefH9-iaaM gene bearing fruits developed by self-pollination ((X)) and without pollination (EM).

FIG. 11 shows a comparison of fruits obtained by self-pollination and without pollination in an eggplant transformed with the DefH9-iaaM gene.

FIG. 12 shows a comparison of fruits in an eggplant transformed with the DefH9-iaaM gene obtained by self-pollination which contains developing seeds and without pollination which does not contain seeds (parthenocarpic).

DETAILED DESCRIPTION OF THE INVENTION

Figure 1:
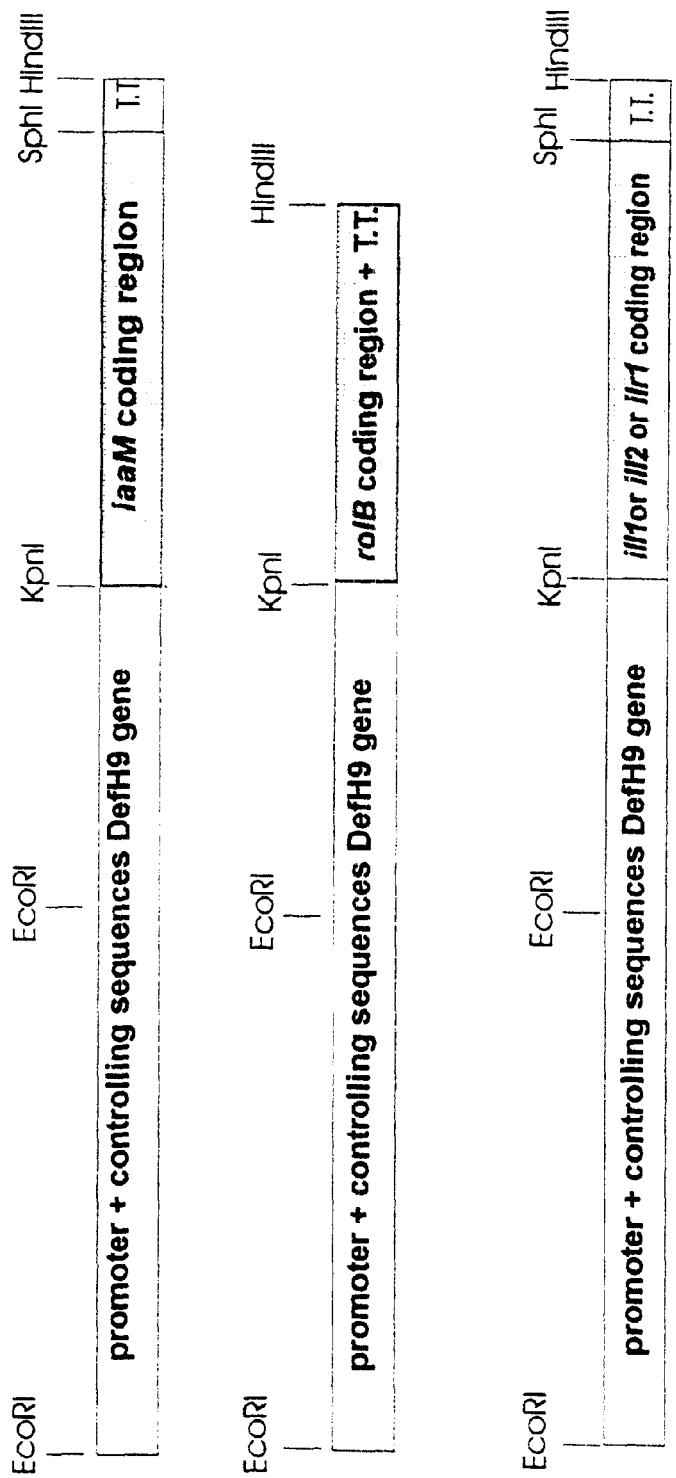
FIG. 1: A schematic representation of the chimeric genes used. DNA sequences from *Antirrhinum majus* provide promoter and regulatory sequences for transcription of coding regions from: (i) the iaaM gene of *Pseudomonas savastanoi;* (ii) the rolB gene of *Agrobacterium rhizogenes;* (iii) ill1, ill2 or ilr1 genes of *Arabidopsis thaliana*. When indicated signals of termination of transcription from the nos gene of *A. tumefaciens* were included.
Figure 3:
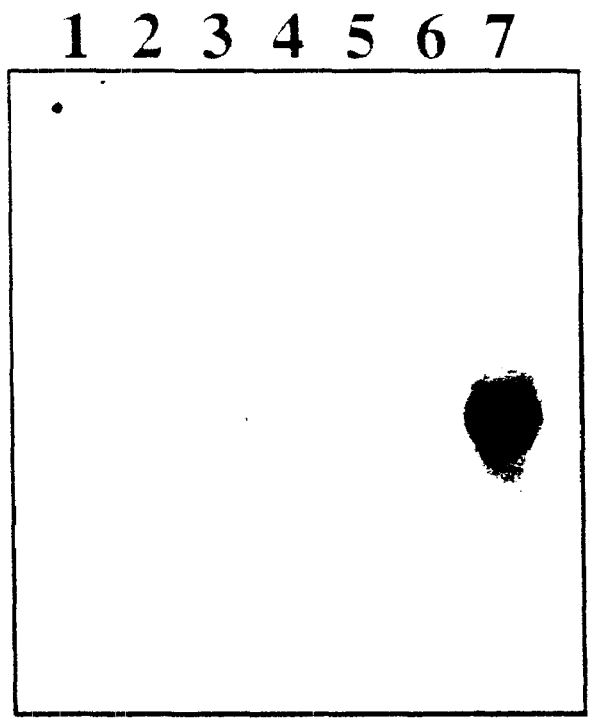
FIG. 3: Northern blot analysis showing the expression of DefH9 mRNA in *Antirrhinum majus*. 2 µg mRNA from various organs were loaded in each lane indicated by numbers. From left to right: seedling (1), leaf (2), bract (3), sepal (4), petal (5), stamen (6) and carpel (7). A hybridization signal is detected only in the case of mRNA extracted from carpel.

In the examples the following materials and methods have been used:

1. Bacterial Strains and Cultures

*E. coli.* cells DH5α were used for propagating the recombinant plasmids. All recombinant plasmids were introduced either by electroporation or by conjugation into *Agrobacterium tumefaciens* strain GV3101 using standard techniques (Koncz and Schell, Mol. Gen. Genet. 204 (1986), 383–396).

2. Construction of Recombinant Plasmids and Constructs

The used recombinant plasmids and constructs were constructed according to established methods (Maniatis et al., Molecular Cloning, a Laboratory Manual, Cold Spring Harbour Laboratory, 1982).

3. Plant Tissue Cultures and Transformation 3.1 Transformation of Tobacco

*Agrobacterium tumefaciens* mediated transformation of tobacco plants cv Petit Havana SR1 were obtained using the leaf-disk method. Leaf-disks were prepared from in vitro-grown plants and pre-cultured for two days in MS (Murashige and Skoog, Physiologia Plantarum 15 (1962), 473–497) basal medium supplemented with 0.5 mg/l thidiazuron and 0.1 mg/l IAA, were dipped for 5 min. in an overnight agrobacteria culture resuspended at 0.1 $OD_{600}$ in liquid MS basal medium containing 200 µM acetosyringone and placed back in the same petri dish. After two days the leaf-disks were cultured in the same medium containing 100 mg/l kanamycin and 500 mg/l cefotaxime and subcultured every three weeks. Developed shoots were rooted in MS hormone-free medium containing 50 mg/l kanamycin. After acclimatization the plants were grown under greenhouse condition.

3.2 Transformation of Eggplant

For transformation the female parent of the F1 eggplant hybrid 'Rimina' released by Istituto Sperimentale per l'Orticoltura was employed. The procedure for eggplant transformation was essentially as described in Rotino and Gleddie (Plant Cell Rep. 3 (1990), 26–29) and Rotino et al. (Proc. VIIIth Meeting on genetics and breeding of Capsicum and eggplant; Rome, Italy, Sep. 7–10, 1992, Capsicum Newsletter, special issue, 295–300) with modifications. Leaf, cotyledon and hypocotyl explants were pre-cultured for two days in MS macro and micro nutrients (Murashige and Skoog, (1962), loc.cit.), Gamborg vitamins (Gamborg et al., Exp. Cell Res. 50 (1968), 151–158), 0.5 $gl^{-1}$ MES, 20 µM acetosyringone supplemented with the growth regulators ($mgl^{-1}$) 0.5 ZEA, 0.3 BAP, 0.2 KIN and 0.1 NAA, media were solidified with 2 $gl^{-1}$ phytagel (Sigma), pH 5.8. For explant infection, an overnight *Agrobacterium tumefaciens* liquid culture was centrifugated and the pellet resuspended at 0.1 $OD_{600}$ density in MS basal medium, 2% glucose, 200 µM acetosyringone pH 5.5. The cut edges of the hypocotyls were cut again and all the explants were infected by dipping in bacteria suspension for 5 min, blotted dry onto sterile filter paper and placed back in the same plates. After 48 h the explants were transferred to selective medium (described above) without acetosyringone and supplemented with 30 $mgl^{-1}$ kanamycin and 500 $mgl^{-1}$ cefotaxime. Shoot-bud differentiation and shoot elongation was achieved by transferring calli with compact green nodules to the same selective medium without NAA. Shoots were rooted and propagated in V3 medium (Chambonnet, "Culture d'anthères in vitro chez trois Solanacees maraichères: le piment (Capsicum annuum), l'aubergine (Solanum melongena), la tomate (lycopersicon esculentum)" (1985) Thèse de Docteur d'Université, Academie de Montpellier) without antibiotics. Transgenic plantlets were grown in the greenhouse.

4. Detection of Parthenocarpic Fruit Development 4.1 In Tobacco

Flowers produced by two inflorescences of each of ten chosen transformed and one untransformed regenerated plants were daily (for one month) emasculated at a length of 2–3 cm and covered with paper bags. Another inflorescence was not emasculated and covered to obtain selfed seeds.

4.2 In Eggplant

Flower buds of transformed and untransformed eggplants were covered with paper bags. For each plant flowers were either emasculated before dehiscence of anther (closed flowers) or manually self-pollinated (opened flowers) and covered with a paper bag. The experiment was carried out at Montanaso Lombardo during the period of November 1996 to January 1997 inside a double plastic greenhouse. This means that the experiment was carried out under short day condition with low natural light intensity without artificial illumination and indoor temperature ranging from about 14° C. to about 22° C. These conditions represent very adverse climatic conditions for eggplant fertilization and fruit development. Inside the greenhouse the average temperature was 16.9° C. which represents very limiting conditions for eggplant fruit setting. More importantly, light duration was only 7 hours per day and its intensity was only 46.4 W/m².

5. DNA Analysis by PCR

Genomic DNA was obtained from leaf tissue according to Doyle and Doyle (1987). 100 ng DNA were analyzed by PCR by using the 5' ATGATTGAACAAGATGGATTG-CACGCAGG 3' (Seq ID No. 2) and 5' GAAGAACTCGT-CAAGAAGGCGATA 3' (Seq ID No. 3) primers which amplified a fragment of 739 bp of the nptII coding region and 5' TCTTGGCTTGTAATGGGGATCC 3' (Seq ID No. 4) and 5' GGGTGAATTAAAATGGTCATACAT 3' (Seq ID No. 5) primers which amplified a fragment of 450 bp of DefH9-iaaM gene. PCR reactions were performed in 25 μl of final volume containing 1× buffer (Perkin Elmer), 100 μM dNPTs, 50 pM of each primers 1 U Taq polymerase. Forty-five cycles at an annealing temperature of 55° C. were employed.

6. RNA Analysis

Flower buds (0.4–0.6 cm long) were harvested, frozen in liquid nitrogen and mRNA was extracted and purified according to well established methods. The complementary cDNA was synthesized by using iaaM specific primers (5' GGGTGAATTAAAATGGTCATACAT 3'; Seq ID No. 5 and 5' TTCTTTGGAACTCGTGTTGAGCTC 3'; Seq ID No. 8) and reverse transcriptase for 1 hour at 45° C. The cDNA was used as template for a first PCR reaction, performed at 53° C. for 35 cycles using the same iaaM specific primer and a primer located in the untranscribed but untranslated leader sequence of DefH9 gene at the 5' end of the intron. An aliquot of this reaction was used as template for a second PCR assay. This assay was performed at a Tm of 55° C. using a "Hot Start" to initiate the assay. The reaction was repeated for 35 cycles. PCR products were analyzed by agarose gel electrophoresis, restriction analysis and DNA Blot with subsequent hybridization. The reaction products were also sequenced.

7. Northern Blot Analysis

Total RNA was extracted from plant organs and tissues as described by Logemann et al. (Anal. Biochem. 163 (1987), 16–20). Poly A+ RNA was isolated from total RNA using oligo d(T) Dynabeads (Dynal) following the protocol of the manufacturer. The amount of RNA was determined spectrophotometrically. 2 μg mRNA were loaded per lane and seperated on a 1.2% agarose gel containing 7% formaldehyde. The RNA was transferred to Hybond N filters (Amersham) by standard techniques (Maniatis et al., loc. cit.). Hybridisation with radioactively labeled probes was overnight at 42° C. in 5×SSPE and 50% formamide. As a probe a 600 bp fragment of the DefH9 cDNA without the conserved MADS box at the 5'end was used to avoid cross-hybridisation with other MADS box RNAs. Signals were detected using Kodak X-OMAT AR5 X-ray films.

EXAMPLE 1

Construction of the Plasmid pPCV002-DefH9-iaaM

The recombinant plasmid pPCV002-DefH9-iaaM was obtained by ligating the EcoRI-KpnI fragment of 3480 (14+2250+1212+4 bp) spanning the promoter (2250 bp) and regulatory sequences (1212 bp) of the gene DefH9 from *Antirrhinum majus* to the KpnI-SphI fragment of 1775 bp (2+53+1671+49) spanning the coding region of the iaaM gene from *Pseudomonas syringae* pv. savastanoi. The iaaM gene has been characterized by Yamada et al. (1985) and the sequence used contains 1773 bp (53+1671+49) from the DraI site located 53 bp before the ATG initiation codon till the SphI site 46 bp after the TAA stop codon. The transcription termination sequences from the nopaline synthase gene of *Agrobacterium tumefaciens* are used at the 3' of the coding region. The DNA sequence used is 222 bp long from the site SphI to the site HindIII, both provided by linker sequences. Consequently, the plasmid pPCV002-DefH9-iaaM obtained possesses the following structural features:

- 2250 bp of the DefH9 promoter from *Antirrhinum majus* (having an EcoRI adapter of 14 bp at the 5' end);
- 1212 bp of regulatory sequences present in the transcribed but untranslated leader sequence of the DefH9 gene from *Antirrhinum majus* (including the intron of 1045 bases);
- 6 bp added by Kpn I linker addition;
- 53 bp of untranslated sequence of the iaaM gene from *Pseudomonas syringae* pv. savastanoi with the nucleotide sequence CTGAGGTACCGAAAGAATCG (Seq ID No. 6) at the fusion site (fusion obtained by adding a KpnI linker)
- 1671 bp of coding region of the iaaM gene from *Pseudomonas syringae* pv. savastanoi;
- 49 bp (46+3 bp of stop codon) of 3' untranslated trailer sequence of the iaaM gene from *Pseudomonas syringae* pv. savastanoi; and
- 222 bp containing transcription termination sequences from the nos gene of Agrobacterium.

EXAMPLE 2

Construction of the Plasmid pPCV002-DefH9-rolB

The recombinant plasmid pPCV002-DefH9-rolB was obtained by ligating the EcoRI-KpnI fragment of 3480 bp spanning the promoter and regulatory sequences of the gene DefH9 from *Antirrhinum majus* to the KpnI-HindIII fragment of 1509 bp (39+774+694+2 extra bases added with the Kpn I linker) spanning the coding sequence of the rolB gene. Consequently, the plasmid pPCV002-DefH9-rolB obtained possesses the following structural features:

- 2250 bp of the DefH9 promoter from *Antirrhinum majus* (having at the 5' an EcoRI adapter of 14 bp);
- 1212 bp of regulatory sequences present in the transcribed but untranslated leader sequence of the DefH9 gene from *Antirrhinum majus* (including the intron of 1045 bases);
- 6 bp added by linker addition;
- 39 bp of untranslated sequence of the rolB gene from *Agrobacterium rhizogenes* Ri plasmid A4 with the nucleotide sequence CTGAGGTACCGGGCACTT (Seq ID No. 7) at the fusion site (fusion obtained by adding a KpnI linker);
- 774 bp of coding region of the rolB gene from *Agrobacterium rhizogenes* Ri plasmid A4; and
- 694 bp of 3' flanking sequences present at the 3' end of the rolB coding region (i.e. 691+3 bp of stop codon)

EXAMPLE 3

The Biological Effect of the DefH9-iaaM Gene in Transgenic Tobacco Plants

Figure 4:
FIG. 4: Comparison of a wild type SR1 tobacco plant (left) and a transgenic DefH9-iaaM parthenocarpic plant (right). The transgenic plant is unmodified in its vegetative growth, i.e. it does not show any modification of the growth habit and flowering.
Figure 5:
FIG. 5: Comparison of a wild type SR1 tobacco plant (left) and a transgenic DefH9-iaaM plant (right) at flowering. The plant transgenic for the DefH9-iaaM gene does not show any modification of the growth habit.
Figure 6:
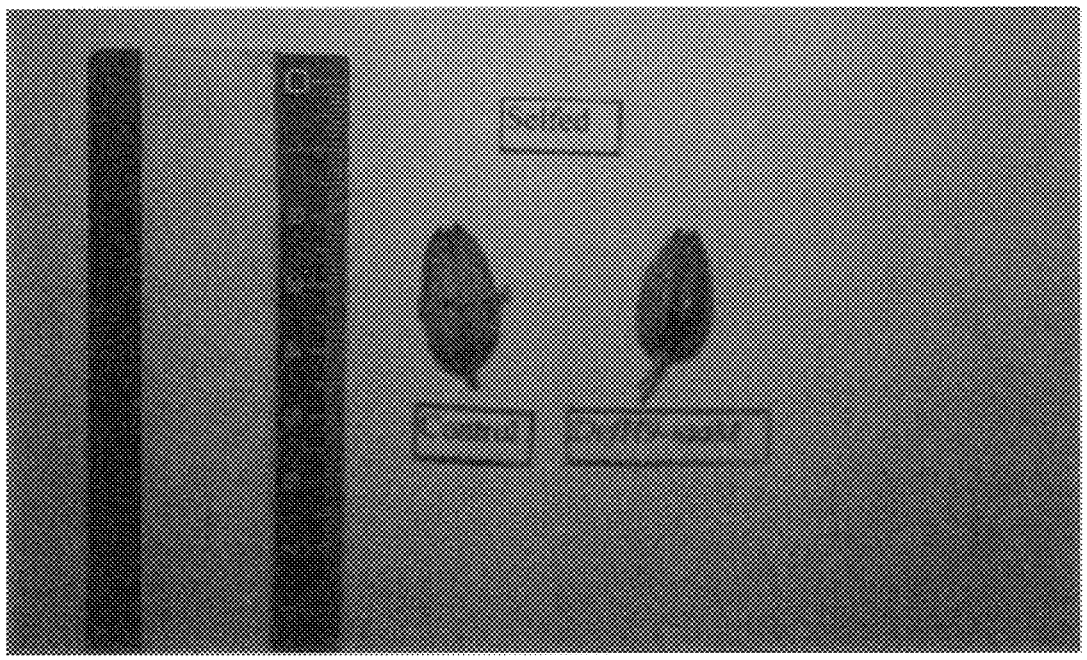
FIG. 6: A comparison of capsules obtained by self-pollination in wild type and DefH9-iaaM tobacco plants. The transgenic plant is able to develop a normal capsule when pollinated.
Figure 7:
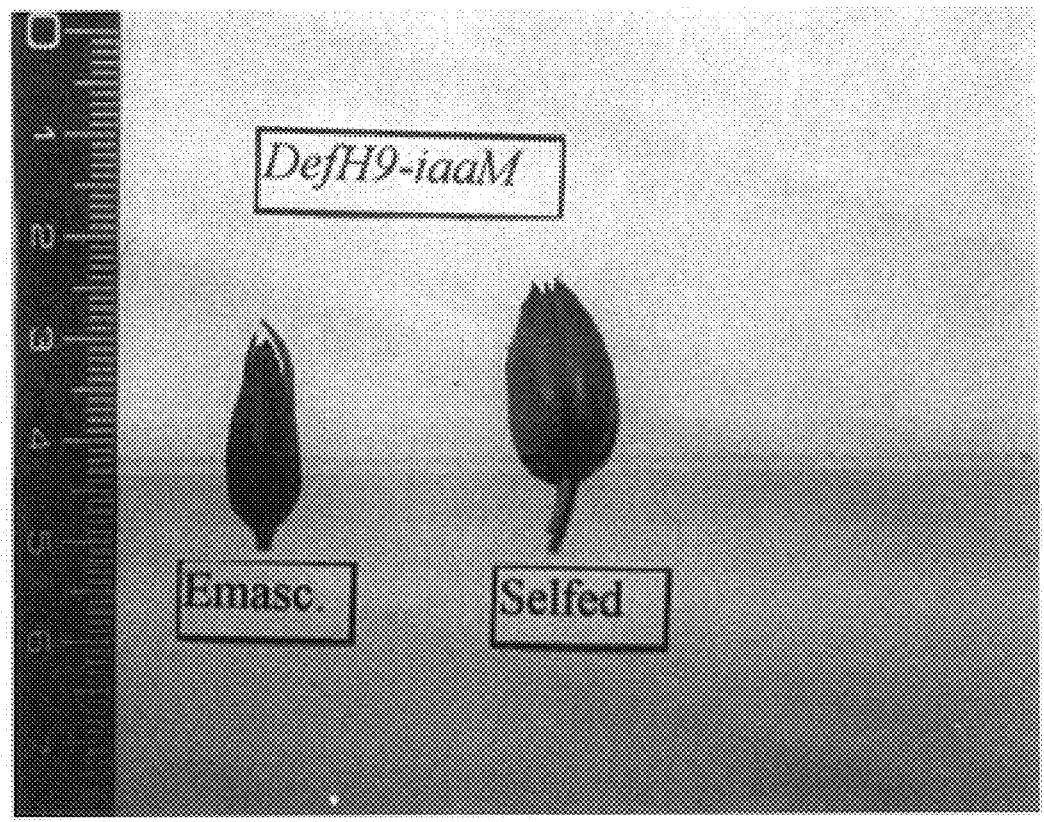
FIG. 7: A comparison of capsules developed by pollination and without pollination (parthenocarpic) in DefH9-iaaM plants. The transgenic plant is able to develop capsules when emasculated, i.e. parthenocarpically. The capsules are seedless.
Figure 8:
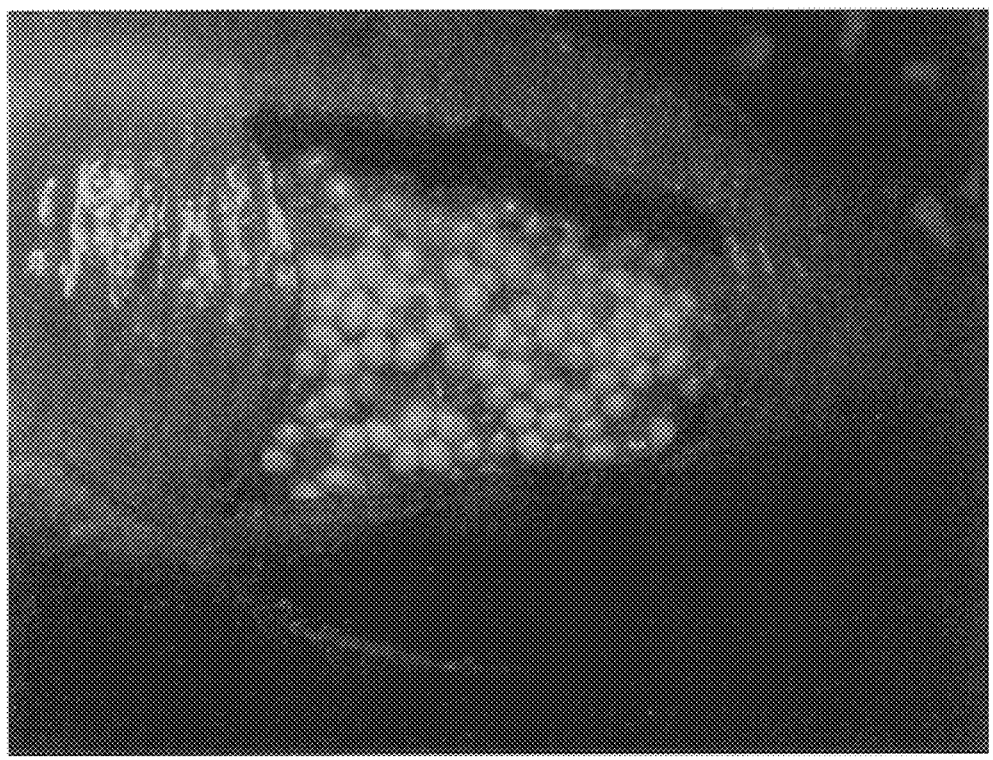
FIG. 8: Capsule from a pollinated DefH9-iaaM transgenic plant. Normal seed development is observed.
Figure 9:
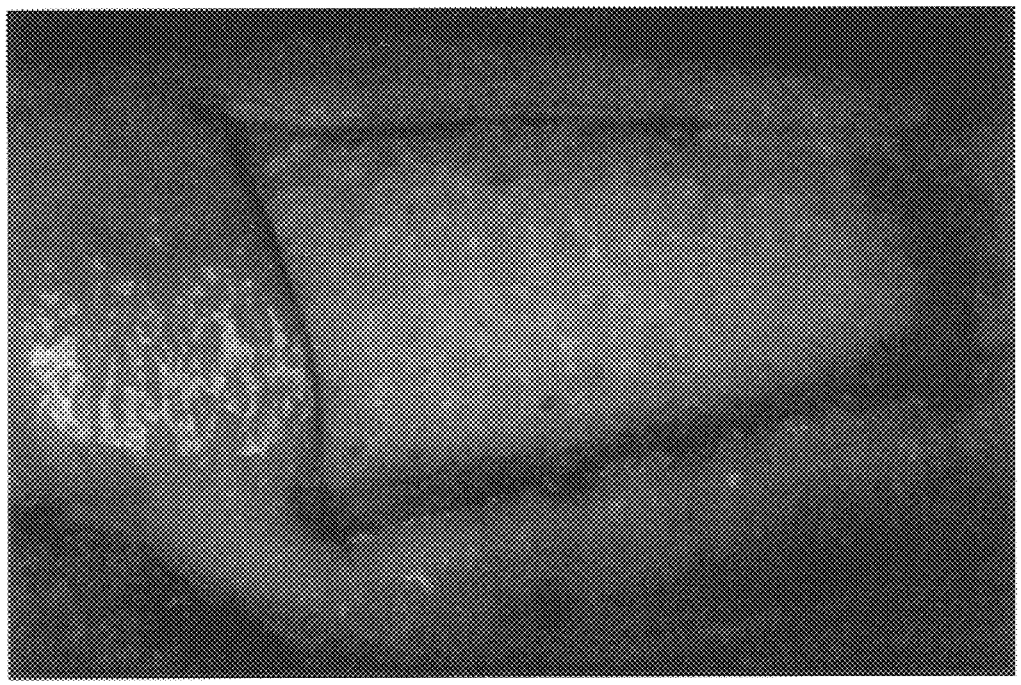
FIG. 9: Capsule from the same plant developed from an emasculated flower. Development of the seeds is not taking place.

Tobacco plants transformed with the DefH9-iaaM construct were analyzed for expression of the iaaM gene. For this purpose RNA was obtained from flower buds of the transgenic plants and analyzed by RT-PCR. The expected product of 168 bp was detected in 10 out of 10 transgenic plants analyzed but not in the negative control (i.e. untransformed tobacco plants). As expected, the fragments contain a Kpn I site as shown by agarose gel electrophoresis and DNA blot analysis. The DNA of the RT-PCR product from one transgenic plant was sequenced. The DNA sequence confirmed that the 168 bp fragment corresponds to the spliced mRNA of the DefH9-iaaM gene. Thus, the transgenic plants expressed the gene in immature flower buds and the pre-mRNA is properly spliced. Tobacco plants transgenic for the DefH9-iaaM gene do not show any alteration of vegetative growth when compared to untransformed tobacco plants (see FIGS. 4 and 5). Moreover, they show normal capsule development when pollinated (see FIG. 6). However, when emasculated, transgenic plants expressing the DefH9-iaaM gene in the flower buds show parthenocarpic development, and consequently seedless capsules (see FIG. 9). Untransformed tobacco plants (and plants not expressing efficiently the DefH9-iaaM gene) do not show parthenocarpic development. The trait is transmitted to the progeny in a mendelian fashion.

EXAMPLE 4
The Biological Effect of the DefH9-rolB Gene

None of the 20 transgenic tobacco plants tested which had been transformed with the DefH9-rolB construct showed parthenocarpic development by itself. However, these plants can be used to increase parthenocarpic development in plants transgenic for the DefH9-iaaM gene either by crossing or by co-introducing the DefH9-rolB and DefH9-iaaM genes.

EXAMPLE 5
The Biological Effect of DefH9-iaaM Gene in Transgenic Eggplants

Figure 10:
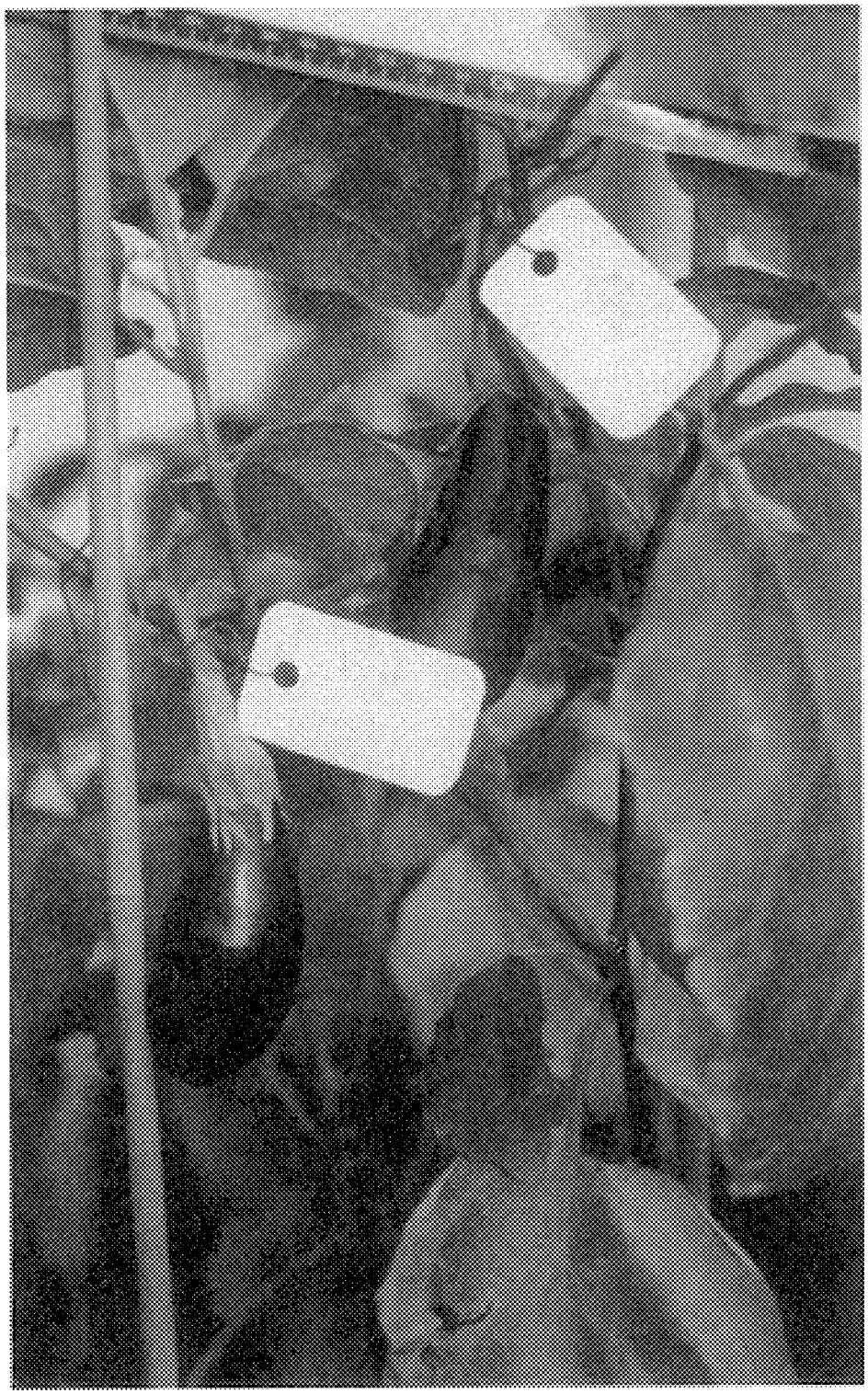
FIG. 10.
Figure 11:
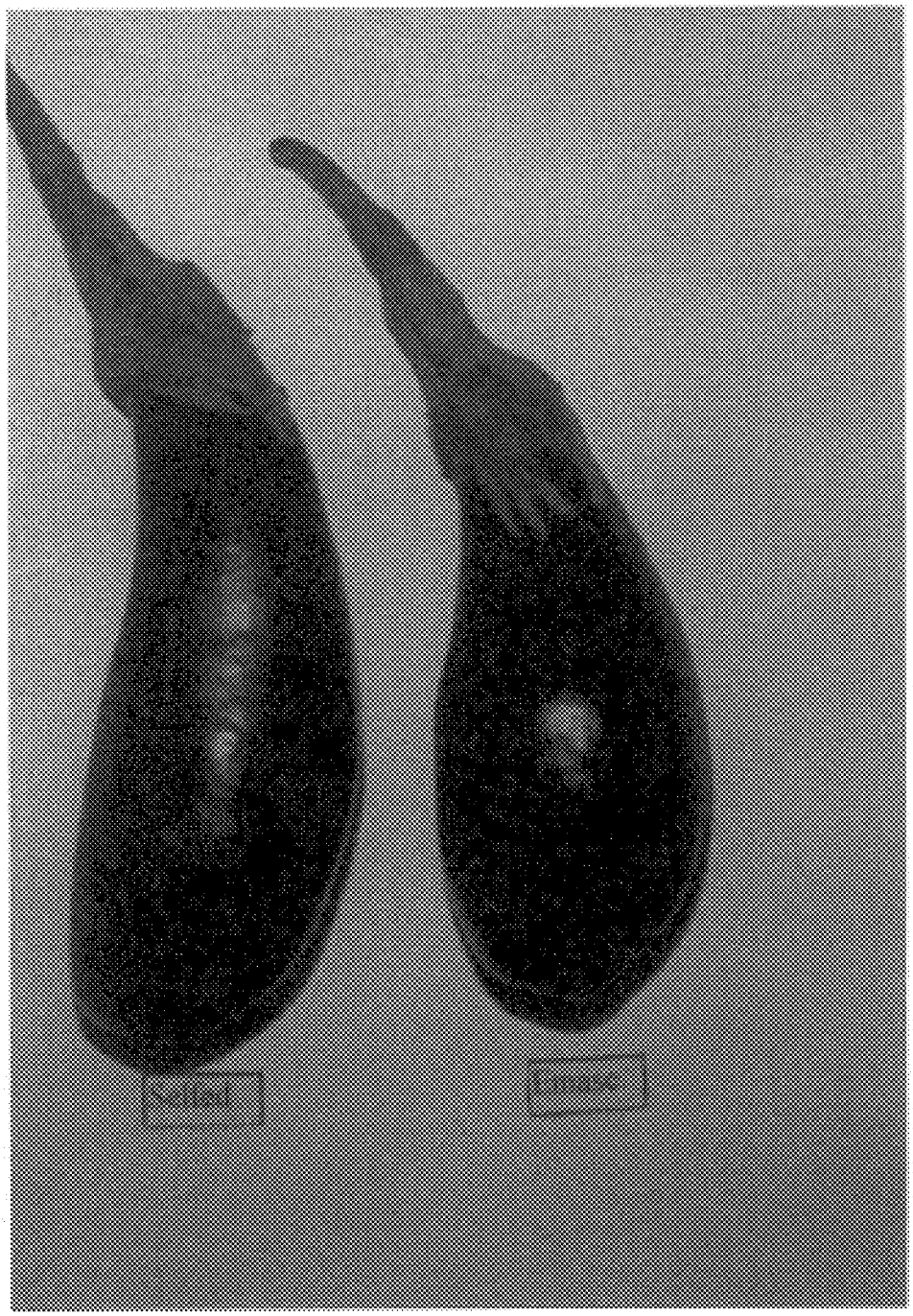
FIG. 11.
Figure 12:
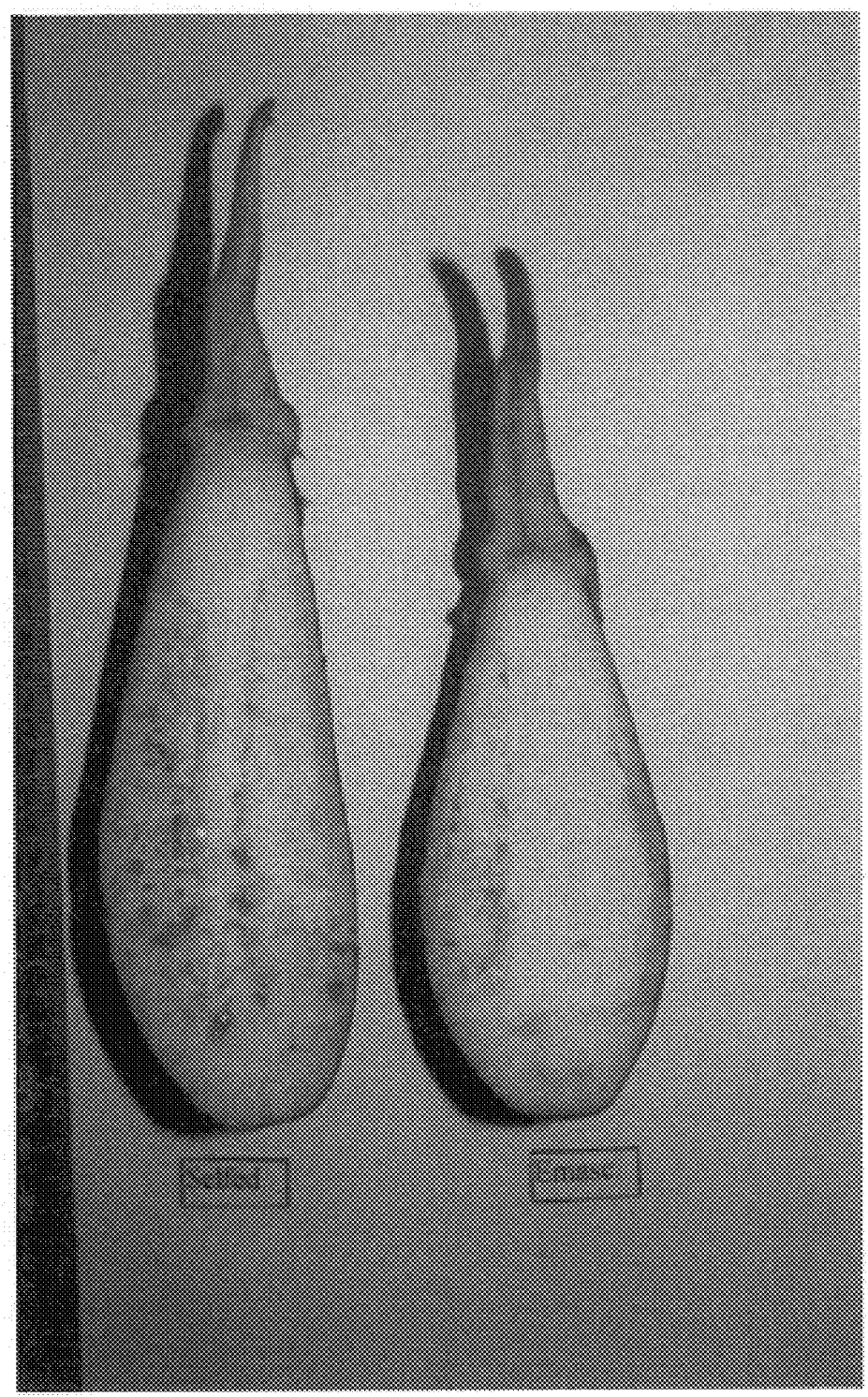
FIG. 12.

Eggplants transgenic for the DefH9-iaaM gene appear phenotypically normal in their vegetative growth and floral morphology. They are indistinguishable from untransformed eggplants. Fruit setting and fruit development was exclusively achieved in the eggplants transgenic for DefH9-iaaM gene (FIG. 10). In fact in the untransformed eggplant both emasculated and hand-pollinated flowers fell down. In transgenic eggplants expressing the DefH9-iaaM gene the size of fruits obtained from emasculated was slightly smaller compared to the fruits obtained from self-pollinated flowers (FIG. 11). In addition, they show parthenocarpic development when emasculated, and consequently seedles fruits (FIG. 12). Since the temperatures used in the experiments were at the minimum value for fruit setting (optimum average temperature is 28 to 30° C.) and the light intensity and duration was below the minimum level (optimum average light intensity is 500–800 W/m$^2$) to allow pollination, fertilization and fruit setting, these experimental data show that the introduction of the DefH9-iaaM gene can permit to avoid exogenous hormone application to plants when grown in adverse climatic conditions. Adverse conditions might be either low temperature and/or low light intensity or high temperature.

We claim:

1. A method for establishing parthenocarpy or enhancing fruit setting and development comprising the steps of:
   a) transforming a plant cell or tissue with a nucleic acid molecule comprising:
      i) a promoter capable of conferring placenta- and/or ovule-specific expression to a DNA sequence operably linked to it, wherein said promoter comprises a nucleic acid sequence that has at least 85% sequence identity to nucleotides 1–2264 of SEQ ID NO: 1; and
      ii) a DNA sequence operably linked to the promoter, wherein the DNA sequence encodes a protein involved in the biosynthesis of an auxin when expressed in plant cells; and
   b) generating a plant comprising the transformed plant cell or tissue.

2. The method of claim 1, wherein the nucleic acid sequence has at least 90% sequence identity to nucleotides 1 to 2264 of SEQ ID NO: 1.

3. The method of claim 2, wherein the nucleic acid sequence has at least 95% sequence identity to nucleotides 1 to 2264 of SEQ ID NO: 1.

4. The method of claim 3, wherein the nucleic acid sequence is nucleotides 1 to 2264 of SEQ ID NO: 1.

5. The method according to claim 1 or 4, wherein said DNA sequence encodes a protein normally not expressed in plant cells.

6. The method according to claim 5, wherein said DNA sequence encodes a bacterial protein.

7. The method according to claim 6, wherein said DNA sequence is the iaaM gene of *Pseudomonas syringae* or a gene coding for a functionally equivalent protein from another organism.

8. A recombinant nucleic acid molecule comprising:
   a) a promoter capable of conferring placenta and/or ovule-specific expression to a DNA sequence operably linked to it, the promoter comprising a nucleic acid sequence having at least 85% sequence identity to nucleotides 1–2264 of SEQ ID NO: 1; and
   b) a DNA sequence operably linked to the promoter, wherein the DNA sequence encodes a protein involved in the biosynthesis of an auxin when expressed in a plant cell.

9. The recombinant nucleic acid molecule of claim 8, wherein the nucleic acid sequence has at least 90% sequence identity to nucleotides 1 to 2264 of SEQ ID NO: 1.

10. The recombinant nucleic acid molecule of claim 9, wherein the nucleic acid sequence has at least 95% sequence identity to nucleotides 1 to 2264 of SEQ ID NO: 1.

11. The recombinant nucleic acid molecule of claim 10, wherein the nucleic acid sequence is nucleotides 1 to 2264 of SEQ ID NO: 1.

12. The recombinant nucleic acid molecule according to claim 8 or 11, wherein the DNA sequence encodes a protein which is normally not expressed in plant cells.

13. The recombinant nucleic acid molecule according to claim 12, wherein the DNA sequence encodes a bacterial protein.

14. The recombinant nucleic acid molecule according to claim 13, wherein the DNA sequence is the iaaM gene of *Pseudomonas syringae* or a gene coding for a functionally equivalent protein from another organism.

15. A host cell transformed with the recombinant nucleic acid molecule according to claim 8 or 11.

16. A plant cell comprising the recombinant nucleic acid molecule according to claim 8 or 11.

17. A plant comprising the plant cell according to claim 16.

18. A part of a plant comprising the plant cell according to claim 16.

19. The part of a plant according to claim 18, which is a fruit, a seed, or other propagation material.

20. The method of claim 1, wherein the nucleic acid sequence has at least 85% sequence identity to SEQ ID NO: 1.

21. The method of claim 20, wherein the nucleic acid sequence has at least 90% sequence identity to SEQ ID NO: 1.

22. The method of claim 21, wherein the nucleic acid sequence has at least 95% sequence identity to SEQ ID NO: 1.

23. The method of claim 22, wherein the nucleic acid sequence is SEQ ID NO: 1.

24. The recombinant nucleic acid molecule of claim 8, wherein the nucleic acid sequence has at least 85% sequence identity to SEQ ID NO:1.

25. The recombinant nucleic acid molecule of claim 24, wherein the nucleic acid sequence has at least 90% sequence identity to SEQ ID NO: 1.

26. The recombinant nucleic acid molecule of claim 25, wherein the nucleic acid sequence has at least 95% sequence identity to SEQ ID NO: 1.

27. The recombinant nucleic acid molecule of claim 26, wherein the nucleic acid sequence is SEQ ID NO: 1.

28. A vector comprising the recombinant nucleic acid molecule according to any one of claim 8, 11 or 27.

29. A host cell comprising the vector according to claim 28.

30. A plant cell comprising the vector according to claim 28.

31. A plant comprising the plant cell according to claim 30.

32. A part of a plant comprising the plant cell according to claim 30.

33. The part of a plant according to claim 32, which is a fruit, a seed, or other propagation material.

* * * * *

UNITED STATES PATENT AND TRADEMARK OFFICE
CERTIFICATE OF CORRECTION

PATENT NO. : 6,483,012 B1
DATED : November 19, 2002
INVENTOR(S) : Angelo Spena et al.

It is certified that error appears in the above-identified patent and that said Letters Patent is hereby corrected as shown below:

<u>Title page,</u>
Item [73], change "Förederung" to -- Förderung --.
Add -- Istituto Sperimentale per L'Orticoltura, Pontecagnano (IT) --.

Signed and Sealed this

Twenty-fourth Day of June, 2003

JAMES E. ROGAN
*Director of the United States Patent and Trademark Office*

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 3480 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Anthirrhinum majus (xi) SEQUENCE DESCRIPTION: SEQ ID NO: 1:

```
AATTCGGCAC GAGGTCCCTT TCTATTTTTG CACAAAGCGT CTTTTACTCG TATCAAGAAT      60

TTGATTCTAC TTTATTACTC AAATTCGTCA CTTCTCTTAC ACACACACAC ACACACACAC     120

ACACACACAC ACACATATAT ATATTACACT CCAGCCCTTT GTATCTATCC CATCTTTCTC     180

TTATTAATGA ATGAACCAAT AAATAGACCT CTAACAAATA CAGTTTGAGC AGGCTGGTTG     240

TTTAATAAAA TTAATGCTGG TTGTTAATTT AAACTGACAT TGTTTTTGCT CAGACACGGC     300

AACCTCTATA GTACAGTTTC TTCTTAGTAT TGAAAATTTA GTTGTGGATT TTTTTTTTAA     360

GAAATACAAT TTACAGCTAT AATGTACAAT GCCAAGAACT ACAGTTATTT TTTTAATCAC     420

TGAAATGCTT ATATATATTA AAAAGAATCT AAAGAGGGTC AGCGCAATTA TTAACTTTTT     480

TCTCCTGAAC ATTGACCAAA CTTAATATGT GAAAACAACA AAAATTCATA AGGCAGAGGG     540

ATCATAGTAC AACATTGGAT TTGGTGTGTT ACATATAATT AATTAGACCA GGTCCCCTCA     600
```

```
GTTACTATTC ATGTAAAACT TGTACTTATT GAGCAGATAT TTCTAAAGCT ATACCCTAAC       660

CAATCAAACT GGACTACGTA CCCTATCCTT TCAAAGGTTT TTTTTTTTTT TTTTTTTTCC       720

TCCCAATTAA ATTCGCGTGC ACAAACAAAA CTATATTAAT CAGGTAAGAA AATTGCGACT       780

CATATAGTTT TCCATGTTAA AAAAAGTGAG ATATACCAAT TAATTTCACT GCATGCAAAC       840

AATATGCATG CCCAAGTAAG TTATGGAAGT TCTTTTTCCT ATATATAGAA ACCAACTTAG       900

CAATCTCTAT TTCATATATA TATATAAACA GTTAATTTAT TAGTCTCTGA AAAAATTTAA       960

TGCAAGTCGA TCGGTTTACA AAAGTATAT  ATGGGCAATT AAATTGGAAC AATAAGTGTC      1020

ACGCTAGTTT TGAATCAGCT CATGATCATG ACAGGATACT CCATAAGTTT TCATTAAATC      1080

TTAGCTGATA TATCTAGTTA GGAGCCGTAG ATATATAAGA AGGTAACGAT TAAATTGAAA      1140

CGATAAGTTA CATATTATAA TATGTCATTT GTATGATTAC TTGATTAGGG TATTAGATTG      1200

TGCAGCCTAA TGTATTGTAC ATTAATTCCC TCCTTTCTAA CACGGTTCAA CTCATGTATA      1260

AAATTTTAGG GGTATTACCG ATAATTCACG TAAAATTATA ATTATGATTG TATTCCTAAT      1320

AAAAATAGTC CACTAATGTA CGCAATTGCA ATTGACTCAT TGAACATATT GAAAAACTCC      1380

CGGTTCGGCA TGCTGCCTCA AGACACGGTC TCTCTAACGA ACCGAATACA CAAATTTATG      1440

TGTGTTTCGT CGCTTTTTGC GTGTACCATA TAATCGGATT GCTTCATAAA GGGAGGTTAA      1500

ATAAACTCTG CTACAATTCA ACCTCAGTAG ATTATTTGAT GCGCCAAGCA ACAACGGTTA      1560

TATTATGCAA CGAAGTACGA GCTTATCAAA TTACATTGTT TCGGGCTCAT ATCTCTAATA      1620

GTCCTACTAA ACCCCGTAAT ATATAGCAAA ATAATAGTAC ACAGATTCAA AAATAAAACC      1680

CCTTAATATG AGGCTACTAT CGACTACCAA AGGTAATACA CATCATAATC AATGTTCCAA      1740

AAACATAATT AAAAACAGTT AATTATATTA AGTCCATGTA GTTTTTAAAA TTAAGAGATA      1800

TATTCAAGTC TCAACAAACA CATGCAAGTT ACATATCTAG TGACTTCTGC GTGTAATGCA      1860

CCTAACAACA AACCCTAACC AGCCAAAACT AAAAAATATA TATATGTAAC ACAGTAACAG      1920

AATATATTCA CCTCCCAAAA TCCCATTATT TATAAGAATT TTTTTAAAGT TCTTGGTAAT      1980

TAATTCCCGC ATGCAAACTC ACCTAATTTT TTTCTATGCT CACCTGGGAT TTAATAATTA      2040

TAAAAAAGAC ATTAAAACAT TTTACAAAGT CATGCAACAA TCCTTTAAAA AAAAAAAAAA      2100

AAAAAGCTGA AGCAATTACT ATATTTGGTG CGAATTCTCC CTGCAGAGCT GATAATAATC      2160

ACACCACGCC TGGTACAAAA ATGGAAATGG TGTCATTTTC TTGGCCAGCT CTTCTATCTC      2220

TCCTTCTTTT GCACTACATA AGATAAAGCT AGGTATATAC AAAGAAAGAA AATAAGTATA      2280

TCAAATAAT  TAGTGGTGTG ATTATTTAAT ATTTATTTGA TCATTCAAGA AACTAAAAAC      2340

TTTGAAGGGA TTCTTTGGAA CTCGTGTTGA GCTCTCAAAA CTCGCCGGAA AATAGAAATA      2400

TTTTCCGAAC AAGACAGGTT TGTGAGTCAT CATGCAGATC ATGAAGATTG TCTAATTATA      2460

TATTAAAAAA GGAATAAATA TTTCTTTAAG TATGGATTGG TTAATTAATT TATTTTTTCC      2520

TCTTTATGTT TATGGCACAG TACCAAATGT TTTCTCTTTG TGCTCAAATT TATGTCAGTT      2580

TTTTTTTGTA TGTTCTTGTT TAAGCATGGA TCTATTGCCA TAACACATAA AACTTGTTTT      2640

TTGGCTTGAA AGATTAATC  TTTCCTCCTA TTTTTTCATG GGTTTTTTTT TTTTTTTTT      2700

TTTTATTCAT TGACAAGAAT GTCAAATCTT TAGTATGATT TTTATTTTTA TTTGTATGCA      2760

TGATTTCAAA AGCTTTTAAT TTGCTATCTT CTAGCGCCAA AAACTTGTTT CTACCCTAGG      2820

GGACTATGGA ACTGAGGGGA ATCTTTGGAA ACTTCTGATT TCATTTTGGG CCTTGTTTGT      2880

TTTTCTGATT TCTTGTTTTT GGAGGGGACT TTTATAAAAT ATGAGCTGTG TAAAGTCGAT      2940

GAAGGAGGTT TTGACTCTGA TCCCTCTTTC AAATTTTGGT TGAGTTAAGC TTTTGAAGTC      3000
```

-continued

```
ATTAAAAAGA GCTATATATA TCACTGCCAA GAACTTTGCC AAATAGTTTC AAGATATAAT    3060

TTTTTTTAGT TCAAAGAACA TAGTTTTTTG ATCTTGGCTT GTAATGGGGA TCCTGCTTTT    3120

TTTTTTTTTT TTTCAGTTCA AATTAATTTC TCATCTTGCT ATTCTTGAGG GGCTAATTAC    3180

AGGATTCTTC AGAAAAAATC ATGTATAAGA TTTTCATTAT CTTTTTGTAC ACTATGTATA    3240

GATTTTCAGC TGATTGTTTA TCAAAGCATC CTCTTCAAAA AGTCTTTCTA TTTTCAAATT    3300

AAAACTATGT CTTCTCTGTG TGTGTTGAAT CAAAAGACTT CCTTTTCTTT TTTTTTGCTA    3360

CAAAGAAAGA AAATCCAGTG TTTGCTTTAG ATCTATGATA CATTGTTCTC TATGATCAAG    3420

ATTAATAAAT CTTATAGTGA GCTTTTTGTT TATTATGATT AGGTTATTTT TCTGAGGTAC    3480
```

(2) INFORMATION FOR SEQ ID NO: 2:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: YES (iv) ANTI-SENSE: NO (xi) SEQUENCE DESCRIPTION: SEQ ID NO: 2:

```
ATGATTGAAC AAGATGGATT GCACGCAGG                                       29
```

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: YES (iv) ANTI-SENSE: NO (xi) SEQUENCE DESCRIPTION: SEQ ID NO: 3:

```
GAAGAACTCG TCAAGAAGGC GATA                                            24
```

(2) INFORMATION FOR SEQ ID NO: 4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: YES (iv) ANTI-SENSE: NO (xi) SEQUENCE DESCRIPTION: SEQ ID NO: 4:

```
TCTTGGCTTG TAATGGGGAT CC                                              22
```

(2) INFORMATION FOR SEQ ID NO: 5:

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: YES (iv) ANTI-SENSE: NO (xi) SEQUENCE DESCRIPTION: SEQ ID NO: 5:

GGGTGAATTA AAATGGTCAT ACAT                                              24

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: YES (iv) ANTI-SENSE: NO (xi) SEQUENCE DESCRIPTION: SEQ ID NO: 6:

CTGAGGTACC GAAAGAATCG                                                   20

(2) INFORMATION FOR SEQ ID NO: 7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: YES (iv) ANTI-SENSE: NO (xi) SEQUENCE DESCRIPTION: SEQ ID NO: 7:

CTGAGGTACC GGGCACTT                                                     18

(2) INFORMATION FOR SEQ ID NO: 8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: YES (iv) ANTI-SENSE: NO (xi) SEQUENCE DESCRIPTION: SEQ ID NO: 8:

TTCTTTGGAA CTCGTGTTGA GCTC                                              24
```